(12) United States Patent
Vendely et al.

(10) Patent No.: US 11,116,505 B2
(45) Date of Patent: *Sep. 14, 2021

(54) APPLICATOR FOR SURGICAL STAPLER BUTTRESS

(71) Applicant: Cilag GmbH International, Zug (CH)

(72) Inventors: Michael J. Vendely, Lebanon, OH (US); Trevor J. Barton, Cincinnati, OH (US); Emily A. Schellin, Cincinnati, OH (US); Mark S. Zeiner, Mason, OH (US)

(73) Assignee: Cilag GmbH International, Zug (CH)

( * ) Notice: Subject to any disclaimer, the term of this patent is extended or adjusted under 35 U.S.C. 154(b) by 12 days.

This patent is subject to a terminal disclaimer.

(21) Appl. No.: 16/235,522

(22) Filed: Dec. 28, 2018

(65) Prior Publication Data

US 2020/0205823 A1 Jul. 2, 2020

(51) Int. Cl.
*A61B 17/072* (2006.01)
*A61B 1/00* (2006.01)

(52) U.S. Cl.
CPC .... *A61B 17/07292* (2013.01); *A61B 1/00087* (2013.01); *A61B 2017/07257* (2013.01);
(Continued)

(58) Field of Classification Search
CPC .... A61B 17/07292; A61B 2017/07271; A61B 2017/07257; A61B 1/00087; A61B 2017/07278
(Continued)

(56) References Cited

U.S. PATENT DOCUMENTS

| 4,805,823 A | 2/1989 | Rothfuss |
| 5,415,334 A | 5/1995 | Williamson, IV et al. |

(Continued)

FOREIGN PATENT DOCUMENTS

EP 3 143 947 A2 3/2017

OTHER PUBLICATIONS

U.S. Appl. No. 16/234,727, entitled "Surgical Stapler with Tissue Engagement Features Around Tissue Containment Pin," filed Dec. 28, 2018.

(Continued)

*Primary Examiner* — Robert F Long
(74) *Attorney, Agent, or Firm* — Frost Brown Todd LLC

(57) ABSTRACT

A buttress applier cartridge assembly includes a buttress assembly and a buttress applier cartridge. The buttress assembly includes a buttress configured to support a staple formed therein as well an adhesive layer for adhering to an end effector. The buttress applier cartridge includes a housing defining a gap extending in a longitudinal direction as well as a platform. The platform extends longitudinally from a proximal portion to a distal portion and is exposed in a transverse direction adjacent to the gap. The proximal and distal portions respectively have a proximal stiffness and a different, distal stiffness in the transverse direction. Thereby, the proximal and distal portions support the buttress assembly thereon to deform with the proximal and distal stiffnesses and provide reactionary forces of at least the predetermined minimum force while receiving the end effector for accommodating various camber orientations of the end effector.

20 Claims, 13 Drawing Sheets

(52) U.S. Cl.
CPC .............. *A61B 2017/07271* (2013.01); *A61B 2017/07278* (2013.01)

(58) Field of Classification Search
USPC .......................................... 227/175.1–182.1
See application file for complete search history.

(56) References Cited

U.S. PATENT DOCUMENTS

| | | | |
|---|---|---|---|
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 6,978,921 B2 | 12/2005 | Shelton, IV et al. | |
| 6,988,650 B2 | 1/2006 | Schwemberger et al. | |
| 7,000,818 B2 | 2/2006 | Shelton, IV et al. | |
| 7,134,587 B2 | 11/2006 | Schwemberger et al. | |
| 7,143,923 B2 | 12/2006 | Shelton, IV et al. | |
| 7,147,139 B2 | 12/2006 | Schwemberger et al. | |
| 7,147,140 B2 | 12/2006 | Wukusick et al. | |
| 7,204,404 B2 | 4/2007 | Nguyen et al. | |
| 7,207,472 B2 | 4/2007 | Wukusick et al. | |
| 7,303,108 B2 | 12/2007 | Shelton, IV | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,524,320 B2 | 4/2009 | Tierney et al. | |
| 7,644,848 B2 | 1/2010 | Swayze et al. | |
| 7,691,098 B2 | 4/2010 | Wallace et al. | |
| 7,721,930 B2 | 5/2010 | McKenna et al. | |
| 7,806,891 B2 | 10/2010 | Nowlin et al. | |
| 8,141,762 B2 | 3/2012 | Bedi et al. | |
| 8,210,411 B2 | 7/2012 | Yates et al. | |
| 8,371,491 B2 | 2/2013 | Huitema et al. | |
| 8,408,439 B2 | 4/2013 | Huang et al. | |
| 8,453,914 B2 | 6/2013 | Laurent et al. | |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,579,990 B2 | 11/2013 | Priewe | |
| 8,602,288 B2 | 12/2013 | Shelton, IV et al. | |
| 8,616,431 B2 | 12/2013 | Timm et al. | |
| 8,783,541 B2 | 7/2014 | Shelton, IV et al. | |
| 8,800,838 B2 | 8/2014 | Shelton, IV | |
| 8,801,735 B2 | 8/2014 | Shelton, IV et al. | |
| 8,814,025 B2 | 8/2014 | Miller et al. | |
| 8,820,605 B2 | 9/2014 | Shelton, IV | |
| 8,844,789 B2 | 9/2014 | Shelton, IV et al. | |
| 8,899,464 B2 | 12/2014 | Hueil et al. | |
| 8,992,060 B2 | 4/2015 | Dassanayake et al. | |
| 8,998,060 B2 | 4/2015 | Bruewer et al. | |
| 9,101,359 B2 | 8/2015 | Smith et al. | |
| 9,186,142 B2 | 11/2015 | Fanelli et al. | |
| 9,198,644 B2 | 12/2015 | Balek et al. | |
| 9,211,120 B2 | 12/2015 | Scheib et al. | |
| 9,301,759 B2 | 4/2016 | Spivey et al. | |
| 9,393,018 B2 | 7/2016 | Wang et al. | |
| 9,398,911 B2 | 7/2016 | Auld et al. | |
| 9,445,808 B2* | 9/2016 | Woodard, Jr. | A61B 17/0401 |
| 9,492,170 B2 | 11/2016 | Bear et al. | |
| 9,517,065 B2 | 12/2016 | Simms et al. | |
| 9,566,061 B2* | 2/2017 | Aronhalt | A61B 17/00491 |
| 9,597,082 B2 | 3/2017 | Stokes et al. | |
| 9,622,746 B2 | 4/2017 | Simms et al. | |
| 9,693,777 B2* | 7/2017 | Schellin | B29C 67/20 |
| 9,717,497 B2 | 8/2017 | Zerkle et al. | |
| 9,783,980 B2* | 10/2017 | Snyder | E04D 11/02 |
| 9,795,379 B2 | 10/2017 | Leimbach et al. | |
| 9,808,248 B2 | 11/2017 | Hoffman | |
| 9,839,421 B2 | 12/2017 | Zerkle et al. | |
| 9,848,871 B2 | 12/2017 | Harris et al. | |
| 9,867,615 B2 | 1/2018 | Fanelli et al. | |
| 9,913,642 B2 | 3/2018 | Leimbach et al. | |
| 9,936,954 B2 | 4/2018 | Shelton, IV et al. | |
| 9,999,408 B2 | 6/2018 | Boudreaux et al. | |
| 10,045,780 B2 | 8/2018 | Adams et al. | |
| 10,092,292 B2 | 10/2018 | Boudreaux et al. | |
| 10,094,405 B2* | 10/2018 | Nonaka | B29C 65/562 |
| D833,010 S | 11/2018 | Harris et al. | |
| 10,123,798 B2 | 11/2018 | Baxter, III et al. | |
| D836,198 S | 12/2018 | Harris et al. | |
| D836,199 S | 12/2018 | Schowalter et al. | |
| 10,172,611 B2* | 1/2019 | Shelton, IV | A61B 17/00491 |
| 10,251,649 B2* | 4/2019 | Schellin | A61B 17/07292 |
| 10,349,939 B2 | 7/2019 | Shelton, IV et al. | |
| 10,433,839 B2* | 10/2019 | Scheib | A61B 17/07207 |
| 2005/0139636 A1 | 6/2005 | Schwemberger et al. | |
| 2005/0143759 A1 | 6/2005 | Kelly | |
| 2005/0145672 A1 | 7/2005 | Schwemberger et al. | |
| 2008/0169328 A1 | 7/2008 | Shelton | |
| 2009/0095791 A1* | 4/2009 | Eskaros | A61B 17/072 227/175.1 |
| 2009/0206126 A1* | 8/2009 | Huitema | A61B 17/07292 227/175.1 |
| 2012/0080340 A1* | 4/2012 | Shelton, IV | A61B 17/00491 206/339 |
| 2012/0241493 A1 | 9/2012 | Baxter, III et al. | |
| 2012/0289979 A1* | 11/2012 | Eskaros | A61B 17/07292 606/151 |
| 2013/0068816 A1 | 3/2013 | Vasudevan et al. | |
| 2013/0075447 A1 | 3/2013 | Weisenburgh, II et al. | |
| 2013/0105548 A1* | 5/2013 | Hodgkinson | A61B 17/072 227/176.1 |
| 2013/0206813 A1 | 8/2013 | Nalagatla | |
| 2013/0256366 A1* | 10/2013 | Shelton, IV | A61B 17/0644 227/175.1 |
| 2014/0239037 A1 | 8/2014 | Boudreaux et al. | |
| 2015/0196299 A1* | 7/2015 | Swayze | A61B 17/0643 227/176.1 |
| 2015/0351758 A1 | 12/2015 | Shelton, IV et al. | |
| 2016/0089146 A1 | 3/2016 | Harris et al. | |
| 2016/0089149 A1* | 3/2016 | Harris | A61B 17/0682 227/176.1 |
| 2016/0278774 A1 | 9/2016 | Shelton, IV et al. | |
| 2017/0027571 A1 | 2/2017 | Nalagatla et al. | |
| 2017/0049444 A1 | 2/2017 | Schellin et al. | |
| 2017/0055980 A1 | 3/2017 | Vendely et al. | |
| 2017/0055981 A1* | 3/2017 | Vendely | A61B 17/07292 |
| 2017/0055982 A1 | 3/2017 | Zeiner et al. | |
| 2017/0055986 A1 | 3/2017 | Harris et al. | |
| 2017/0056016 A1 | 3/2017 | Barton et al. | |
| 2017/0056017 A1 | 3/2017 | Vendely et al. | |
| 2017/0056018 A1 | 3/2017 | Zeiner et al. | |
| 2017/0086823 A1 | 3/2017 | Leimbach et al. | |
| 2017/0086837 A1 | 3/2017 | Vendely et al. | |
| 2017/0086842 A1 | 3/2017 | Shelton, IV et al. | |
| 2018/0235610 A1 | 8/2018 | Harris et al. | |
| 2018/0235611 A1 | 8/2018 | Harris et al. | |
| 2018/0235619 A1 | 8/2018 | Harris et al. | |
| 2019/0000481 A1 | 1/2019 | Harris et al. | |
| 2020/0205807 A1* | 7/2020 | Bakos | A61B 17/0682 |

OTHER PUBLICATIONS

U.S. Appl. No. 16/234,740, entitled "Surgical Stapler with Sloped Staple Deck for Varying Tissue Compression," filed Dec. 28, 2018.
U.S. Appl. No. 16/235,473, entitled "Adhesive Distribution on Buttress for Surgical Stapler," filed Dec. 28, 2018.
U.S. Appl. No. 16/235,488, entitled "Configuration of Buttress for Surgical Stapler," filed Dec. 28, 2018.
U.S. Appl. No. 16/235,503, entitled "Surgical Stapler Buttress with Tissue In-Growth Promotion," filed Dec. 28, 2018.

(56) References Cited

OTHER PUBLICATIONS

U.S. Appl. No. 16/235,541, entitled "Packaging for Surgical Stapler Buttress," filed Dec. 28, 2018.
U.S. Appl. No. 16/235,617, entitled "Method of Applying Buttresses to Surgically Cut and Stapled Sites," filed Dec. 28, 2018.
U.S. Appl. No. 16/235,630, entitled "Curved Tip Surgical Buttress Applicator with Opening Feature for Curved Tip Alignment," filed Dec. 28, 2018.
U.S. Appl. No. 16/235,670, entitled "Curved Tip Surgical Buttress Assembly Applicator with Proximal Alignment Features," filed Dec. 28, 2018.
U.S. Appl. No. 16/235,681, entitled "Curved Tip Surgical Buttress Assembly Applicator with Compression Layer Pocket Features," filed Dec. 28, 2018.
Design U.S. Appl. No. 29/675,045, entitled "Surgical Stapler Deck with Tissue Engagement Cleat Features," filed Dec. 28, 2018.
Design U.S. Appl. No. 29/675,047, entitled "Surgical Stapler Deck with Tissue Engagement Recess Features," filed Dec. 28, 2018.
Design U.S. Appl. No. 29/675,168, entitled "Applicator for Surgical Stapler Buttress," filed Dec. 28, 2018.
Design U.S. Appl. No. 29/675,170, entitled "Buttress for Surgical Stapler," filed Dec. 28, 2018.
Design U.S. Appl. No. 29/675,172, entitled "Tray for Surgical Stapler Buttress Applicator," filed Dec. 28, 2018.
Design U.S. Appl. No. 29/675,197, entitled "Applicator for a Stapler Buttress," Dec. 28, 2018.
Design U.S. Appl. No. 29/675,199, entitled "Buttress Assembly for a Surgical Stapler," filed Dec. 28, 2018.
U.S. Appl. No. 62/209,041, entitled "Method and Apparatus for Applying a Buttress to End Effector of a Surgical Stapler," filed Aug. 24, 2015.
European Search Report, Partial, and Provisional Written Opinion, dated Mar. 27, 2020 for Application No. EP 19219463.7, 11 pgs.
European Search Report, Extended, and Written Opinion, dated Jul. 13, 2020 for Application No. EP 19219463.7, 10 pgs.
International Search Report and Written Opinion dated Jun. 23, 2020 for Application No. PCT/IB2019/060821, 13 pgs.

\* cited by examiner

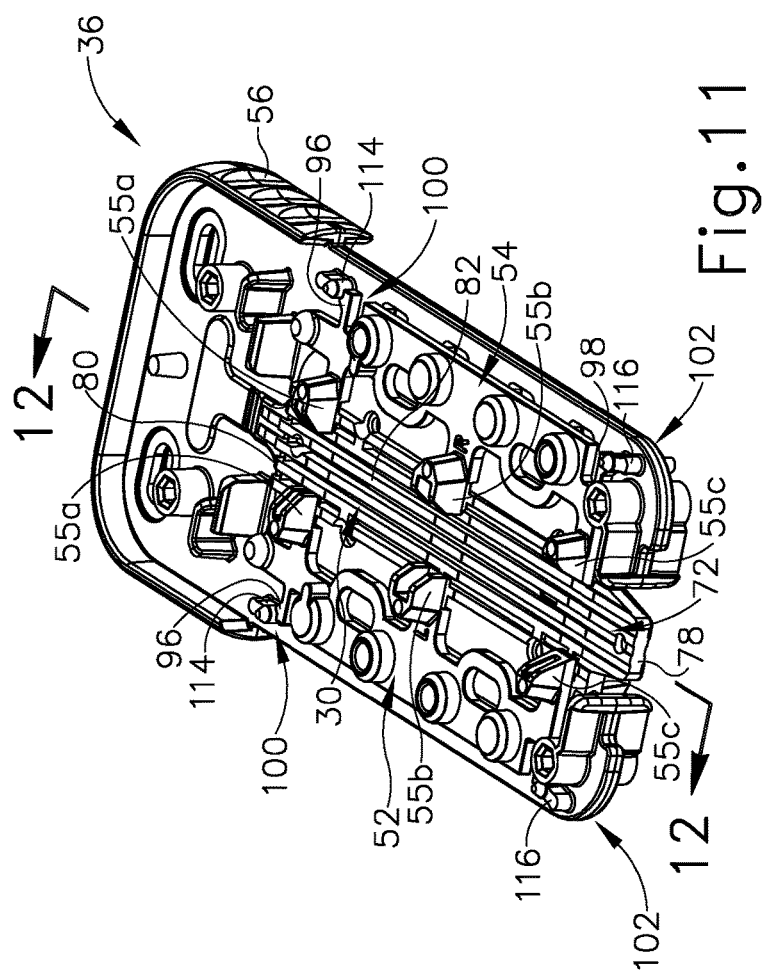
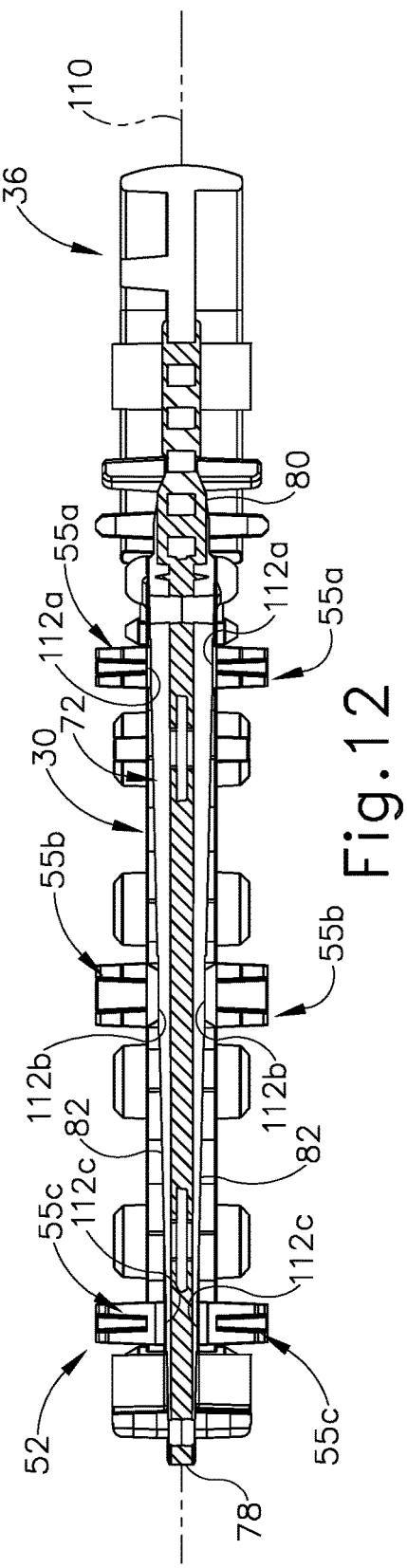
Fig.11
Fig.12

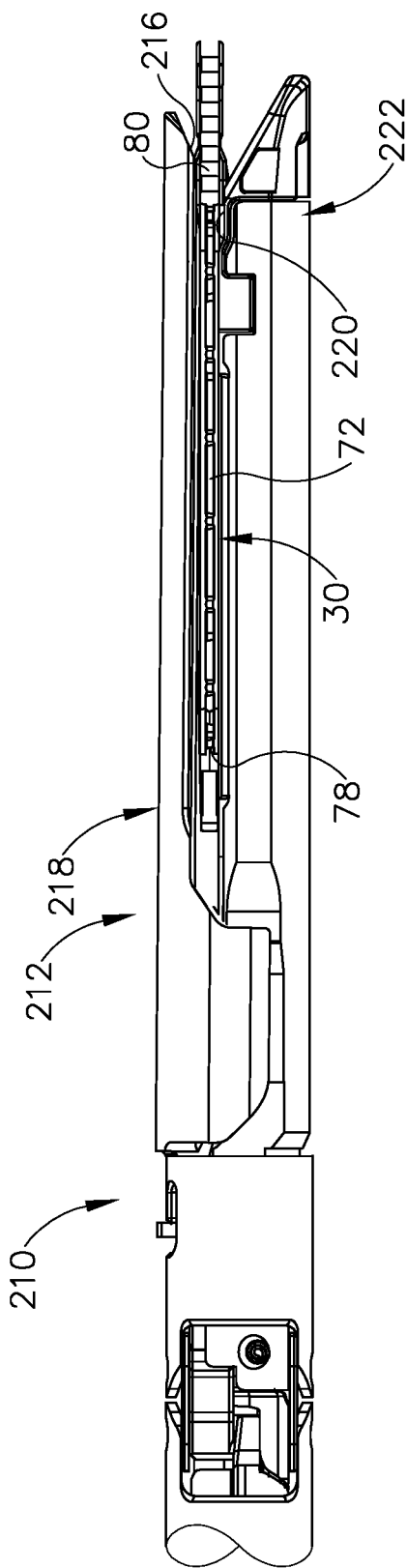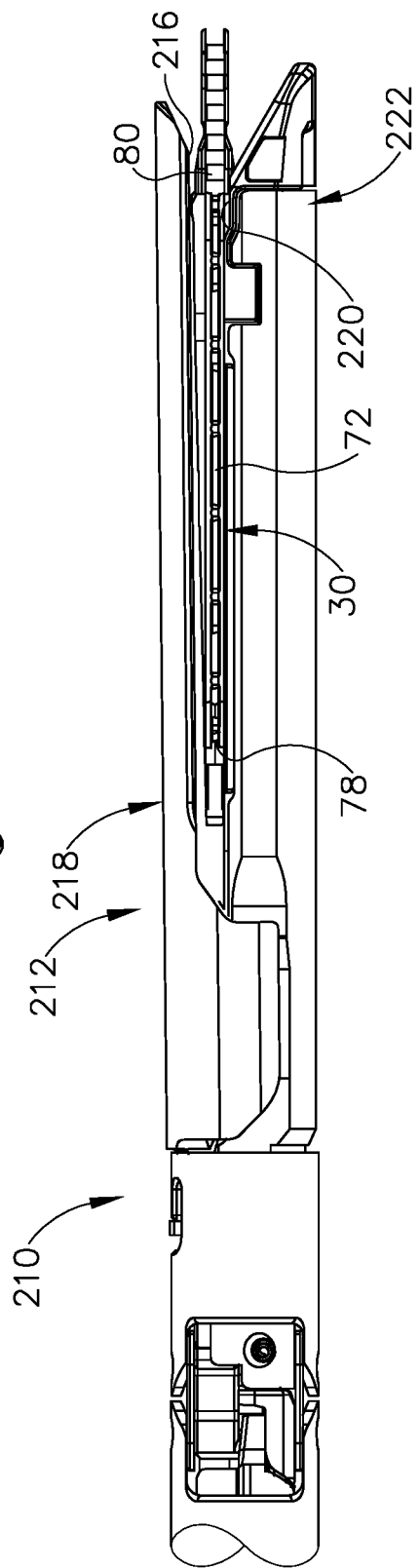

APPLICATOR FOR SURGICAL STAPLER BUTTRESS

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited for use through a thoracotomy are disclosed in U.S. Pat. No. 9,186,142, entitled "Surgical Instrument End Effector Articulation Drive with Pinion and Opposing Racks," issued Nov. 17, 2015; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,839,421, entitled "Jaw Closure Feature for End Effector of Surgical Instrument," issued Dec. 12, 2017; U.S. Pat. No. 9,867,615, entitled "Surgical Instrument with Articulation Lock having a Detenting Binary Spring," issued Jan. 16, 2018; U.S. Pat. No. 9,622,746, entitled "Distal Tip Features for End Effector of Surgical Instrument," issued Apr. 18, 2017; U.S. Pat. Pub. No. 2014/0239037, entitled "Staple Forming Features for Surgical Stapling Instrument," published Aug. 28, 2014, issued as U.S. Pat. No. 10,092,292 on Oct. 9, 2018; U.S. Pat. No. 9,795,379, entitled "Surgical Instrument with Multi-Diameter Shaft," issued Oct. 24, 2017; and U.S. Pat. No. 9,808,248, entitled "Installation Features for Surgical Instrument End Effector Cartridge," issued Nov. 7, 2017. The disclosure of each of the above-cited U.S. Patent Publications is incorporated by reference herein.

Additional surgical stapling instruments are disclosed in U.S. Pat. No. 8,801,735, entitled "Surgical Circular Stapler with Tissue Retention Arrangements," issued Aug. 12, 2014; U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued Feb. 12, 2013; U.S. Pat. No. 9,597,082, entitled "Method and Apparatus for Sealing End-to-End Anastomosis" Mar. 21, 2017; U.S. Pat. No. 9,398,911, entitled "Rotary Powered Surgical Instruments with Multiple Degrees of Freedom," issued Jul. 26, 2016; U.S. Pat. Pub. No. 2013/0206813, entitled "Linear Stapler," published Aug. 15, 2013, now abandoned; U.S. Pat. Pub. No. 2008/0169328, entitled "Buttress Material for Use with a Surgical Stapler," published Jul. 17, 2008, now abandoned; U.S. Pat. No. 9,848,871, entitled "Woven and Fibrous Materials for Reinforcing a Staple Line," issued Dec. 26, 2017; U.S. Pat. No. 9,936,954, entitled "Devices and Methods for Sealing Staples in Tissue," issued Apr. 10, 2018; and U.S.

Pat. Pub. No. 2016/0089146, entitled "Circular Fastener Cartridges For Applying Radially Exapndable Fastener Lines" published Mar. 31, 2016, issued as U.S. Pat. No. 10,426,476 on Oct. 1, 2019. The disclosure of each of the above-cited U.S. Patents, U.S. Patent Publications, and U.S. Patent Applications is incorporated by reference herein.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples. Such buttress material may be applied to the surgical stapling instrument with a buttress applier cartridge. The buttress applier cartridge retains the buttress material prior to application and releases the buttress material once applied to the surgical stapling instrument. An example of such buttress applier cartridge is disclosed in U.S. Pat. Pub. No. 2017/0056016, entitled "Surgical Stapler Buttress Applicator with End Effector Actuated Release Mechanism," published Mar. 2, 2017, issued as U.S. Pat. No. 10,342,542 on Jul. 9, 2019, the disclosure of which is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 11 depicts a perspective view of the chassis and the platform of FIG. 3 with pairs of left and right actuator sleds of FIG. 7 and FIG. 9;

FIG. 12 depicts a cross-sectional view of the chassis, the platform, and the actuator sleds of FIG. 11 taken along section line 12-12 of FIG. 11;

FIG. 19 depicts the side sectional view of the end effector and the platform of the buttress applier cartridge similar to FIG. 15, but with the end effector in an exemplary over-camber orientation; and FIG. 20 depicts the side sectional view of the end effector and the platform of the buttress applier cartridge similar to FIG. 15, but with the end effector in an exemplary under-camber orientation.

Figure 1:
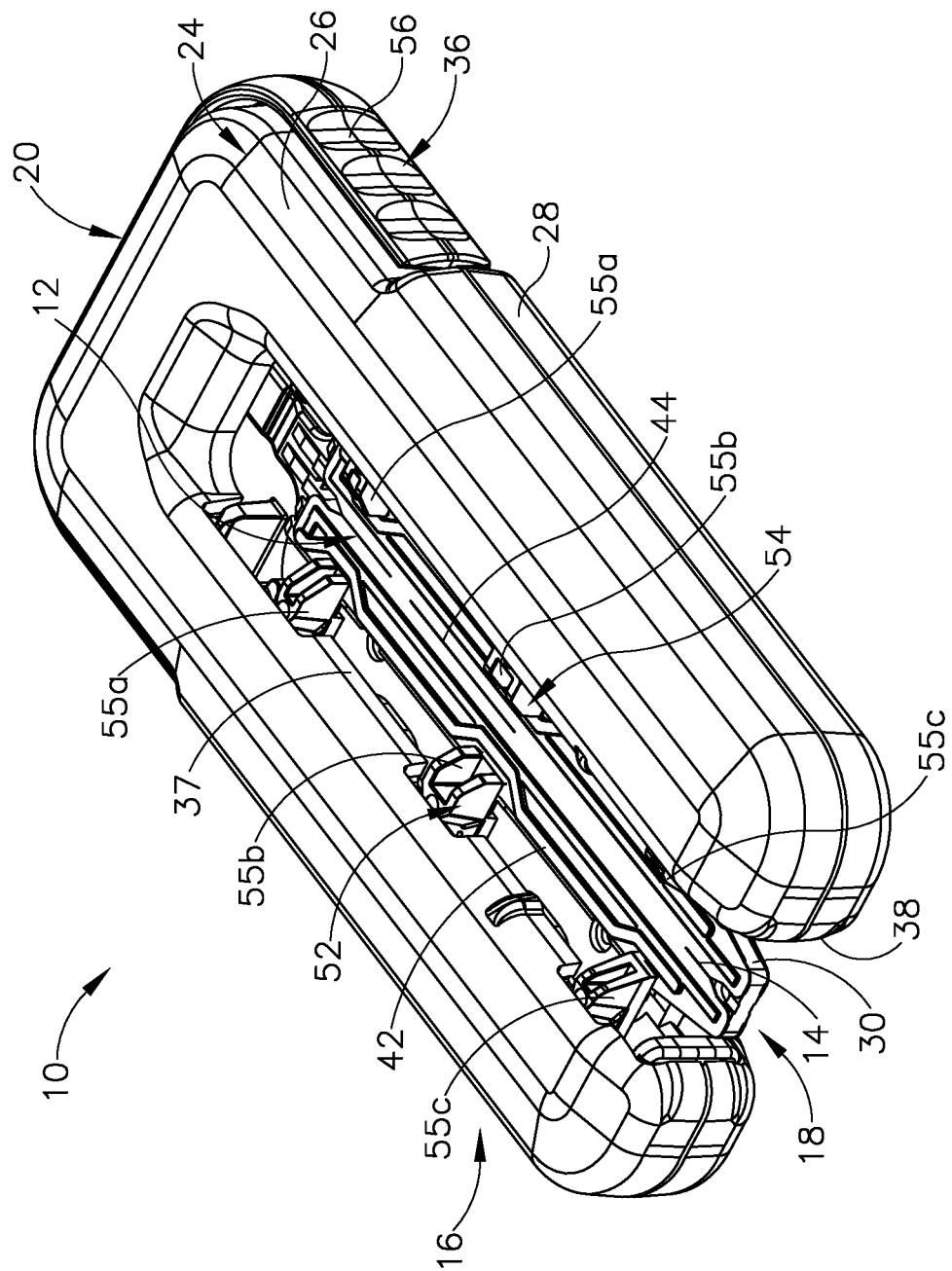
FIG. 1 depicts a perspective view of an exemplary buttress applier cartridge assembly that includes an example of a buttress applier cartridge carrying an example of a buttress assembly for an upper jaw and an example of another buttress assembly for a lower jaw.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It should be understood that terms such as "proximal" and "distal" are used herein with reference to a clinician gripping a surgical instrument, such as surgical and severing instrument (210) and buttress applier cartridge assembly (10) discussed below. It will be further appreciated that for convenience and clarity, spatial terms such as "left," "right," "front," "rear," "upright," "upside-down," "upper," "lower," "bottom," and "top" are used herein with respect to the drawings. However, surgical instruments are used in many orientations and positions, and these terms are not intended to be limiting and absolute.

I. Exemplary Buttress Applier Cartridge Assembly

In some instances, it may be desirable to use an exemplary buttress applier cartridge assembly (10) as shown in FIG. 1 to equip a surgical instrument with a buttress assembly (12) for forming staples in tissue with a buttress (14). Such buttress (14) inhibits the formed staples from pulling through the tissue to thereby reduce a risk of tissue tearing at or near the site of formed staples. In addition to or as an alternative to providing structural support and integrity to a line of staples, buttress (14) may provide various other kinds of effects such as spacing or gap-filling, administration of therapeutic agents, and/or other effects. Prior to use with the surgical instrument, one or more buttresses (14) is releasably retained on a buttress applier cartridge (16), which is configured to deposit buttress assembly (10) onto surgical instrument for use as discussed below in more detail in an exemplary surgical instrument (18) (see FIG. 10A).

FIG. 1 shows buttress applier cartridge assembly (10) including a pair of buttress assemblies (12) releasably retained on buttress applier cartridge (16), which supports and protects buttress assemblies (12) prior to use and further aids with loading buttress assemblies (12) on surgical instrument (210) (see FIG. 10A). Buttress applier cartridge (16) of the present example includes an open end (18) and a closed end (20). Open end (18) is configured to receive end effector (212) (see FIG. 10A) as described below in greater detail. Buttress applier cartridge (16) further includes a housing assembly (24) having an upper housing (26) and a lower housing (28), which each generally define a "U" shape to present open end (18). Various components are interposed between upper and lower housings (26, 28). In particular, these components include a platform (30) supporting a chassis (36).

Platform (30) of the present example supports upper buttress assembly (12) on one side of platform (30) and lower buttress assembly (12) on the other side of platform (30). Platform (30) is exposed in recesses that are formed between the prongs of the "U" configuration of upper and lower housings (26, 28). Thus, upper housing (26) has an upper gap (37) extending to the open end (18) along an upper surface of platform (30), and lower housing (28) similarly has a lower gap (38) extending to the open end (18) along the lower surface of platform (30). The location of platform (30) and buttress assemblies (12) in such recesses may prevent inadvertent contact between buttress assemblies (12) and other devices in the operating room. In other words, upper and lower housings (26, 28) may provide some degree of physical shielding of buttress assemblies (12) while buttress assemblies are retained on platform (30).

Additional features may be combined as applicable with the following example of buttress applier cartridge assembly (10). Such features are described in U.S. patent application Ser. No. 16/235,473, entitled "Adhesive Distribution on Buttress for Surgical Stapler," filed on Dec. 28, 2018, published as U.S. Pub. No. 2020/0046350 on Feb. 13, 2020; U.S. patent application Ser. No. 16/235,503, entitled "Surgical Stapler Buttress with Tissue In-Growth Promotion," filed on Dec. 28, 2018, published as U.S. Pub. No. 2020/0205822 on Jul. 2, 2020; U.S. patent application Ser. No. 16/235,488, entitled "Configuration of Buttress for Surgical Stapler," filed on Dec. 28, 2018, published as U.S. Pub. No. 2020/0205821 on Jul. 2, 2020; U.S. patent application Ser. No. 16/235,541, entitled "Packaging for Surgical Stapler Buttress," filed on Dec. 28, 2018, published as U.S. Pub. No. 2020/0205824 on Jul. 2, 2020; U.S. patent application Ser. No. 16/235,617, entitled "Method of Applying Buttresses to Surgically Cut and Stapled Sites," filed on Dec. 28, 2018, issued as U.S. Pat. No. 11,033,269 on Jun. 15, 2021; U.S. patent application Ser. No. 16/235,630, entitled "Curved Tip Surgical Stapler Buttress Assembly Applicator with Opening Feature for Curved Tip Alignment," filed on Dec. 28, 2018, published 2020/0205826 on Jul. 2, 2020; U.S. patent application Ser. No. 16/235,670, entitled "Curved Tip Surgical Stapler Buttress Assembly Applicator with Proximal Alignment Features," filed on Dec. 28, 2018, issued as U.S. Pat. No. 10,905,424 on Feb. 2, 2021; and U.S. patent application Ser. No. 16/235,681, entitled "Curved Tip Surgical Stapler Buttress Assembly Applicator with Compression Layer Pocket Feature," filed on Dec. 28, 2018, published as U.S. Pub. No. 2020/0205807 on Jul. 2, 2020; U.S. patent application Ser. No. 29/675,168, entitled "Applicator for a Surgical Stapler Buttress," filed on Dec. 28, 2018, issued as U.S. Pat. No. D901,686 on Nov. 10, 2020; U.S. patent application Ser. No. 29/675,170, entitled "Buttress for Surgical Stapler," filed on Dec, 28, 2018; patent application Ser. No. 29/675,172, entitled "Tray for Surgical Stapler Buttress Applicator," filed on Dec. 28, 2018, issued as U.S. Pat. No. D922,576 on Jun. 15, 2021; U.S. patent application Ser. No. 29/675,197, entitled "Applicator for a Surgical Stapler Buttress," filed on Dec. 28, 2018, issued as U.S. Pat. No. D903,115 on Nov. 24, 2020; and U.S. patent application Ser. No. 29/675,199, entitled "Buttress Assembly for a Surgical Stapler," filed on Dec. 28, 2018, the disclosures of which are hereby incorporated by reference.

A. Exemplary Buttress Assembly

With respect to FIG. 1, upper and lower buttress assemblies (12) are structurally identical, but for the relative positions of upper and lower buttress assemblies (12) retained on buttress applier cartridge (16). Buttress applier cartridge assembly (10) may thus be used in more than one orientation with surgical instrument (210) (see FIG. 14A). It will be appreciated that the following description of upper buttress assembly (12) similarly applies to lower buttress assembly (12) but for the respective orientations.

Upper buttress assembly (12) includes buttress (14) and an upper adhesive layer (42). Buttress (14) of the present example more particularly has a three-layer, polymer construction including a core layer sandwiched between two outer layers to be collectively strong yet flexible to support a line of staples. In the present example, core layer is a polyglactin 910 material, which is manufactured and sold by Ethicon, Inc. of Somerville, N.J. as VICRYL, whereas each outer layer is a polydioxanone (PDO) film material. Buttress (14) of the present example is formed by laminating core layer between outer layers under a predetermined pressure, a predetermined temperature, and a predetermine time. Buttress (14) is further mechanically cut to size thereby inhibiting abrasive edges, such as burrs and/or delamination, that could damage sensitive tissues. It will be appreciated that alternative methods of cutting buttresses (14), such as a laser cutting or hot knife cutting, may be similarly used.

By way of further example only, each buttress (14) may comprise one or more of the following: NEOVEIL absorbable PGA felt by Gunze Limited, of Kyoto, Japan; SEAMGUARD polyglycolic acid: trimethylene carbonate (PGA: TMC) reinforcement material by W.L. Gore & Associates, Inc., of Flagstaff, Ariz.; PERI-STRIPS DRY with VERITAS Collagen Matrix (PSDV) reinforcement material, by Baxter Healthcare Corporation of Deerfield, Ill.; BIODESIGN biologic graft material by Cook Medical, Bloomington, Ind.; and/or SURGICEL NU-KNIT hemostat material by Ethicon, Inc. of Somerville, N.J. Still other suitable materials that may be used to form each buttress (14) will be apparent to those of ordinary skill in the art in view of the teachings herein.

In addition or in the alternative, each buttress (14) may comprise a material including, for example, a hemostatic agent such as fibrin to assist in coagulating blood and reduce bleeding at the severed and/or stapled surgical site along tissue. As another merely illustrative example, each buttress (14) may comprise other adjuncts or hemostatic agents such as thrombin may be used such that each buttress (14) may assist to coagulate blood and reduce the amount of bleeding at the surgical site. Other adjuncts or reagents that may be incorporated into each buttress (14) may further include but are not limited to medical fluid or matrix components. Merely illustrative examples of materials that may be used to form each buttress (14), as well as materials that may be otherwise incorporated into each buttress (14), are disclosed in U.S. patent application Ser. No. 14/667,842, entitled "Method of Applying a Buttress to a Surgical Stapler," filed Mar. 25, 2015, issued as U.S. Pat. No. 10,349,939 on Jul. 16, 2019, the disclosure of which is incorporated by reference herein. Alternatively, any other suitable materials may be used.

By way of further example only, each buttress (14) may be constructed in accordance with at least some of the teachings of U.S. Pat. Pub. No. 2012/0241493, entitled "Tissue Thickness Compensator Comprising Controlled Release and Expansion," published Sep. 27, 2012, issued as U.S. Pat. No. 10,123,798 on Nov. 13, 2018, the disclosure of which is incorporated by reference herein; U.S. Pat. Pub. No. 2013/0068816, entitled "Surgical Instrument and Buttress Material," published Mar. 21, 2013, now abandoned, the disclosure of which is incorporated by reference herein; U.S. Pat. No. 9,999,408, entitled "Surgical Instrument with Fluid Fillable Buttress," issued Jun. 19, 2018, the disclosure of which is incorporated by reference herein; U.S. Pat. No. 8,814,025, entitled "Fibrin Pad Matrix with Suspended Heat Activated Beads of Adhesive," issued Aug. 26, 2014, the disclosure of which is incorporated by reference herein; U.S. Pat. No. 8,899,464, entitled "Attachment of Surgical Staple Buttress to Cartridge," issued Dec. 2, 2014, the disclosure of which is incorporated by reference herein; U.S. Pat. No. 9,492,170, entitled "Device for Applying Adjunct in Endoscopic Procedure," issued Nov. 15, 2016, the disclosure of which is incorporated by reference herein; U.S. Pat. No. 8,998,060, entitled "Resistive Heated Surgical Staple Cartridge with Phase Change Sealant," issued Apr. 7, 2015, the disclosure of which is incorporated by reference herein; U.S. Pat. No. 9,393,018, entitled "Surgical Staple Assembly with Hemostatic Feature," issued Jul. 19, 2016, the disclosure of which is incorporated by reference herein; U.S. Pat. No. 9,101,359, entitled "Surgical Staple Cartridge with Self-Dispensing Staple Buttress," issued Aug. 11, 2015, the disclosure of which is incorporated by reference herein; U.S. Pat. No. 9,198,644, entitled "Anvil Cartridge for Surgical Fastening Device," issued Dec. 1, 2015, the disclosure of which is incorporated by reference herein; U.S. Pat. Pub. No. 2013/0075447, entitled "Adjunct Therapy for Applying Hemostatic Agent," published Mar. 28, 2013, now abandoned, the disclosure of which is incorporated by reference herein; U.S. Pat. No. 9,211,120, entitled "Tissue Thickness Compensator Comprising a Plurality of Medicaments," issued Dec. 15, 2015, the disclosure of which is incorporated by reference herein; U.S. Pat. Pub. No. 2015/0351758, entitled "Adjunct Materials and Methods of Using Same in Surgical Methods for Tissue Sealing," published Dec. 10, 2015, issued as U.S. Pat. No. 10,172,611 on Jan. 8, 2019, the disclosure of which is incorporated by reference herein; U.S. Pat. Pub. No. 2017/0049444, entitled "Implantable Layers for a Surgical Instrument," published Feb. 23, 2017, issued as U.S. Pat. No. 10,835,249 on Nov. 17, 2020, the disclosure of which is incorporated by reference herein; U.S. Pat. Pub. No. 2017/0055986, entitled "Medicant Eluting Adjuncts and Methods of Using Medicant Eluting Adjuncts," published Mar. 2, 2017, issued as U.S. Pat. No. 10,569,071 on Feb. 25, 2020, the disclosure of which is incorporated by reference herein; U.S. Pat. Pub. No. 2017/0086837, entitled "Compressible Adjunct with Crossing Spacer Fibers," published Mar. 30, 2017, issued as U.S. Pat. No. 10,433,846 on Oct. 8, 2019, the disclosure of which is incorporated by reference herein; and/or U.S. Pat. Pub. No. 2017/0086842, entitled "Method for Applying an Implantable Layer to a Fastener Cartridge," published Mar. 30, 2017, the disclosure of which is incorporated by reference herein.

Furthermore, buttress (14) is configured to be cut by a knife (not shown) from a proximal portion of buttress (14), along an intermediate portion of buttress (14), and further through a distal portion of buttress (14) such that inward edges are adjacent to cut tissue as discussed below in more detail. Buttress (14) further includes a longitudinally extending pre-cut slit (44) configured to receive knife (not shown) and aid in separating lateral portions of buttress (14) as inward edges form therealong.

Figure 14A:
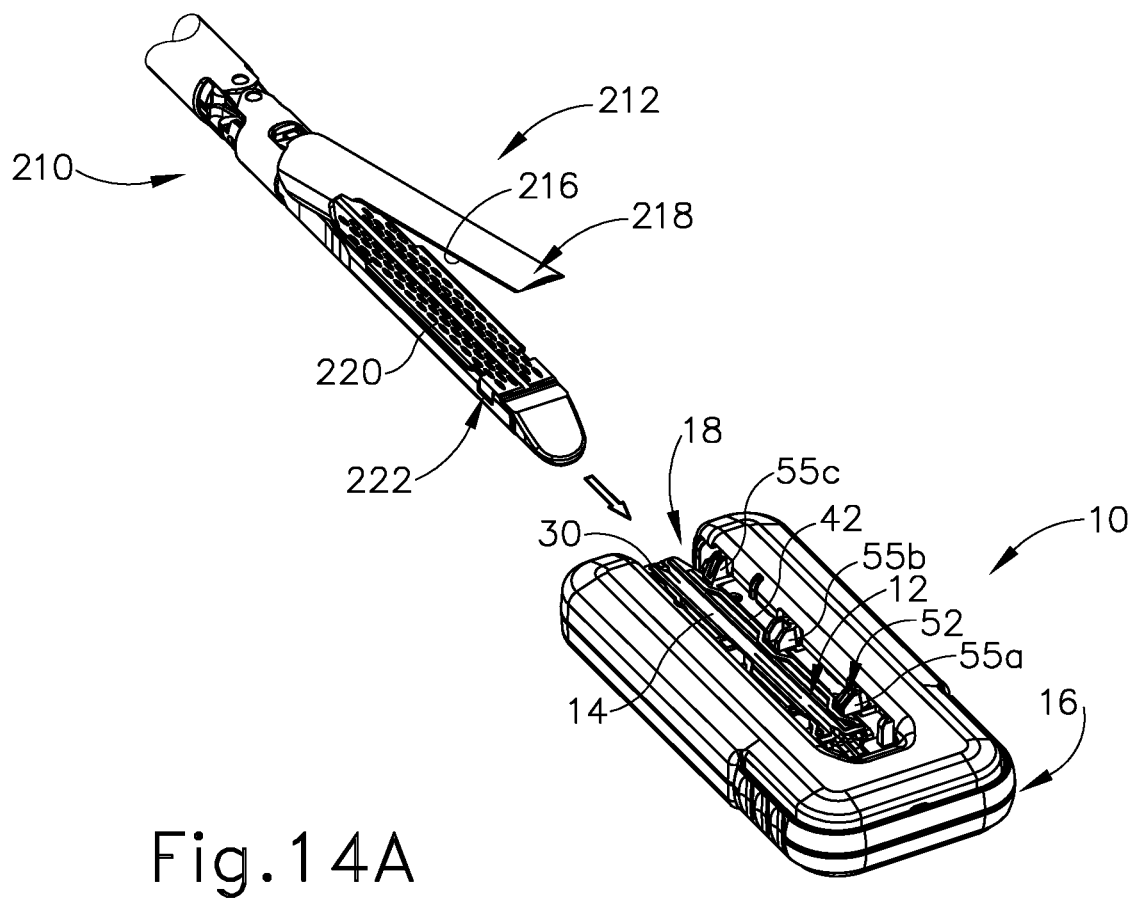
FIG. 14A depicts a perspective view of an end effector of an exemplary surgical instrument showing the buttress applier cartridge assembly of FIG. 1 approaching the end effector with the upper and lower jaws in an open position.

Upper adhesive layer (42) is provided on outer layer of buttress (14) in order to adhere buttress (14) within effector (212) (see FIG. 14A) of surgical instrument (210) (see FIG. 14A). Adherence of the buttress (14) can occur through a variety of mechanisms including but not limited to a pressure sensitive adhesive. In the case of pressure sensitive adhesion, adhesion occurs upon the application of at least a predetermined minimum force. In some versions, each adhesive layer (42) includes a pressure sensitive adhesive material. Examples of various suitable materials that may be used to form adhesive layers (42) are disclosed in U.S. Pat. Pub. No. 2016/0278774, entitled "Method of Applying a Buttress to a Surgical Stapler," published Sep. 29, 2016, issued as U.S. Pat. No. 10,349,939 on Jul. 16, 2019, the disclosure of which is incorporated by reference herein. Alternatively, any other suitable materials may be used. As shown in the present example, adhesive layer (42) is applied to form a continuous outer seal to enhance longevity once applied to end effector (212) (see FIG. 14A).

It should be understood that the term "adhesive," as used herein, may include (but is not limited to) tacky materials and also materials that are pliable or wax-like and adhere to a complex geometry via deformation and conformance.

Some suitable adhesives may provide such pliability to adhere to a complex geometry via deformation and conformance without necessarily providing a high initial tack. In some instances, adhesives with lower tackiness may be removed more cleanly from surfaces. Various suitable materials that may be used to form adhesive layers (42) will be apparent to those of ordinary skill in the art in view of the teachings herein.

B. Exemplary Buttress Applier Cartridge

Figure 2:
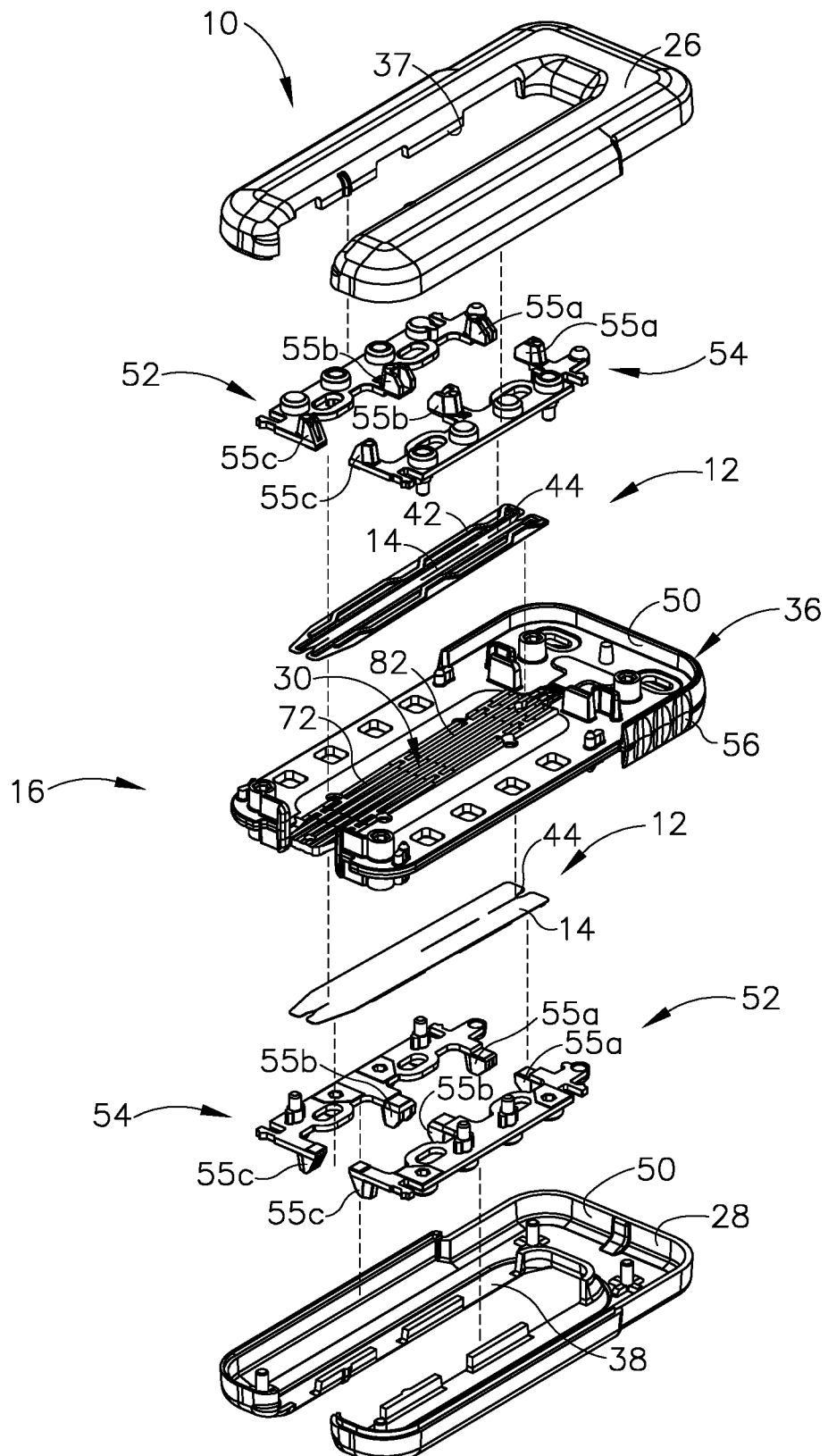
FIG. 2 depicts an exploded perspective view of the buttress applier cartridge assembly of FIG. 1 including a chassis and a platform in addition to a pair of buttress assemblies.

As shown in FIG. 2, buttress applier cartridge (16) includes chassis (36) supporting platform (30) as well as upper and lower housings (26, 28) of housing assembly (24) configured to connect together to define an interior space (50). An upper left actuator sled (52) and an upper right actuator sled (54) are movably connected to an upper face chassis (36) within interior space (50), while a lower left actuator sled (52) and a lower right actuator sled (54) are movably connected to a lower face of chassis (36) within interior space (50). Upper right and left actuator sleds (52, 54) retain upper buttress assembly (12) on platform (30) in a restraint position, but are configured to move from the restraint position to a release position for depositing the upper buttress assembly (12) on end effector (212) (see FIG. 14A). Similarly, lower right and left actuator sleds (52, 54) retain lower buttress assembly (12) on platform (30) in the restraint position, but are configured to move from the restraint position to the release position for depositing the lower buttress assembly (12) on end effector (212) (see FIG. 14A). In the present example, left actuator sled (52) is distinct from right actuator sled (54) for reasons discussed below in greater detail. Also, upper and lower right actuator sleds (52) are structurally identical to each other, and upper and lower left actuator sleds (54) are structurally identical to each other. Thus, upper and lower actuator sleds (52, 54) are interchangeable in this respect and any discussion contained herein directed to a pair of upper actuator sleds (52, 54) is similarly applicable to a pair of lower actuator sleds (52, 54).

Each actuator sled (52, 54) includes a plurality of arms (55a, 55b, 55c) extending laterally inward to selectively and releasably secure buttress assemblies (12) to platform (30). In particular, FIG. 2 show arms (55a, 55b, 55c) positioned such that buttress assemblies (12) are interposed between the free ends of arms (34) and platform (30). Arms (55a, 55b, 55c) are movable laterally outwardly such that arms (55a, 55b, 55c) disengage buttress assemblies (12) as shown in FIG. 2, thereby enabling buttress assemblies (12) to be removed from platform (30). In the present example, arms (55a, 55b, 55c) are configured to bear against buttress assemblies (12) in the restraint position, thereby pinching buttress assemblies (12) against platform (30). Other suitable ways in which arms (5) may engage buttress assemblies (12) will be apparent to those of ordinary skill in the art in view of the teachings herein.

Chassis (36) is configured to cooperate with upper and lower housings (26, 28) to provide a mechanical ground for moving components of buttress applier cartridge (16) and provide structural support for components of buttress applier cartridge (16). Chassis (36) further includes integral gripping features (56) that are exposed on opposite sides of housing assembly (24). Gripping features (56) have a surface geometry configured to promote an operator's grip of buttress applier cartridge (16) during use of buttress applier cartridge (16). Various suitable configurations that may be used for gripping features (56) will be apparent to those of ordinary skill in the art in view of the teachings herein. Similarly, various surface treatments (e.g., elastomeric material, etc.) that may be applied to gripping features (56) will be apparent to those of ordinary skill in the art in view of the teachings herein.

Figure 3:
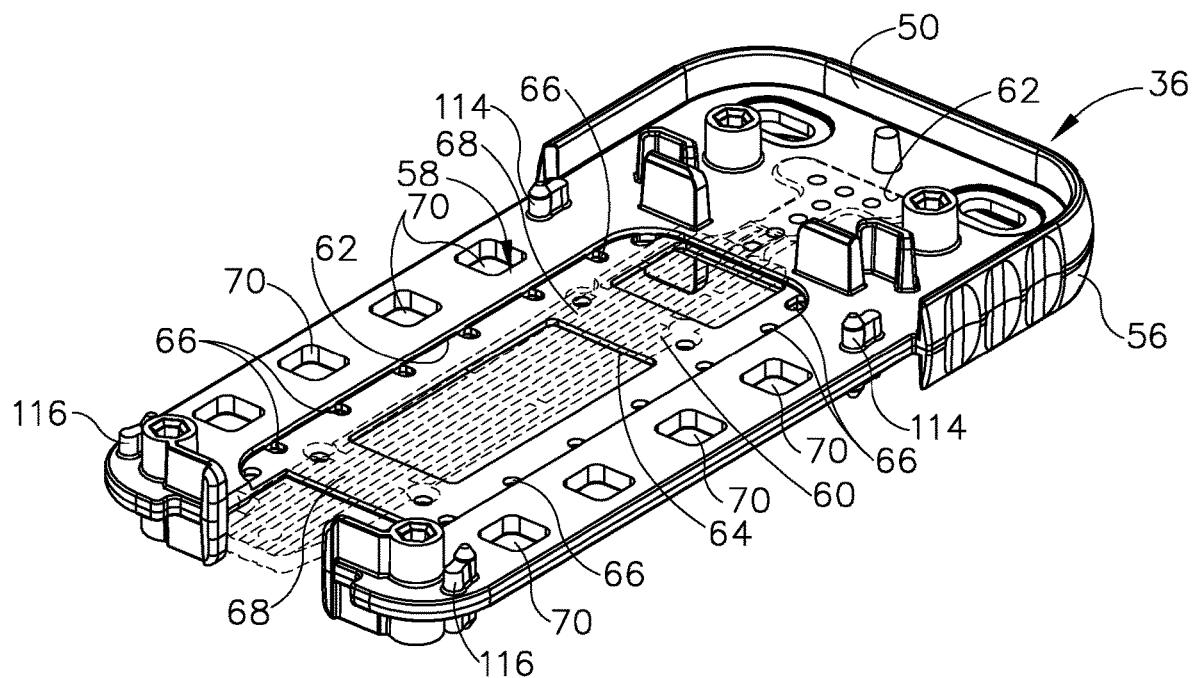
FIG. 3 depicts a perspective view of the chassis with the platform of FIG. 2.

With respect to FIG. 3, platform (30) is connected to and supported by chassis (36) to secure platform (30) relative to upper and lower housing (26, 28) (see FIG. 2). In the present example, platform (30) is unitarily formed and molded to a rigid web portion (58) including a frame (60) and defining a plurality of holes (62, 64, 66) configured provide material overlap for mold securement. Holes (62, 64, 66) more particularly include an upper and a lower peripheral recess (62) to the centrally located frame (60). A central slot (64) extends through frame (60) as well as a plurality of through holes (66) spaced laterally about central slot (64). Frame (60) also extends laterally across central slot (64) at bridge portions (68) to provide additional structural rigidity to chassis (36) while providing platform (30) with sufficient clearance for resilient deformation as discussed below in greater detail. Thereby, recess (62), central slot (64), and through holes (66) receive a resilient, elastomeric material to form and secure the material as platform (30) to chassis (36). While the present platform (30) is molded to chassis (36), it will be appreciated that platform (30) may be alternatively secured to chassis (36), and the invention is not intended to be limited to the particular rigid web portion (58) and molding as discussed herein. Various suitable materials and structural configurations that may be used to form platform (30) will be apparent to those of ordinary skill in the art in view of the teachings herein.

Chassis (36) further includes a plurality of sled clearance holes (70) arranged in a pair of rows on opposing lateral sides of chassis (36). Left and right actuator sleds (52, 54) (see FIGS. 7-10) connect together on opposing sides of chassis (36) through such sled clearance holes (70) to slide inwardly together in connected pairs. Additional details regarding connection and actuation of left and right actuator sleds (52, 54) (see FIGS. 7-10) will be discussed below in greater detail. However, it will be appreciated that any such hole through chassis (36) to provide for fastening clearance of left and right actuator sleds (52, 54) (see FIGS. 7-10) may be used, and the invention is not intended to be unnecessarily limited to sled clearance holes (70) as discussed herein.

i. Exemplary Varying Stiffness Platform for Supporting Buttress Assemblies

FIGS. 3-6 show one example of platform (30) in additional detail as including a pad (72) having a peripheral securement (74) laterally extending therefrom and an anchor securement (76) distally extending therefrom. Collectively, peripheral and anchor securements (74, 76) are positioned in recesses (62) and extend into through holes (66) to secure pad (72) to chassis (36). In some versions, platform (30) is formed of a material that provides a high coefficient of friction, thereby reducing any tendency that buttress assemblies (12) might otherwise have to slide along corresponding surfaces of platform (30). For instance, platform (30) may comprise a resilient, elastomeric material, such as silicone, to be molded to be formed as both securements (74, 76) and pad (72). One example silicone material is a 30 Durometer, Shore A silicone. To this end, pad (72) is formed with varying stiffness along its longitudinal length to simultaneously provide sufficient reactionary forces of at least the predetermined minimum force for adhesion while accommodating a parallel-camber orientation, an over-camber orientation, and an under-camber orientation of end effector (212) (see FIG. 14A) as discussed below in greater detail. As used herein, the term "parallel-camber orientation" refers to an upper jaw and a lower jaw of an end effector being functionally parallel to each other. The term "over-camber orientation" refers to an upper jaw of an end effector being over rotated relative a lower jaw of an end effector. The term "under-camber orientation" refers to an upper jaw being under rotated relative to a lower jaw of an end effector. Exemplary upper and lower jaws will be described in this context below in greater detail.

Figure 4:
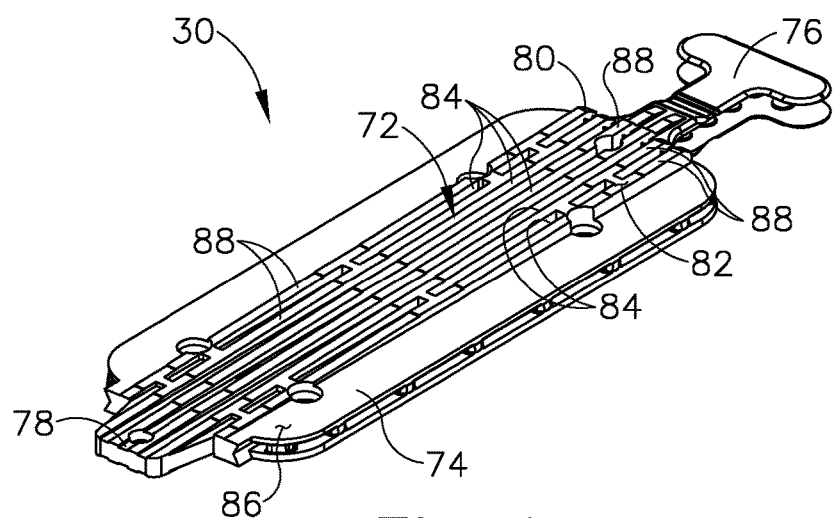
FIG. 4 depicts a front perspective view of the platform of FIG. 2.
Figure 5:
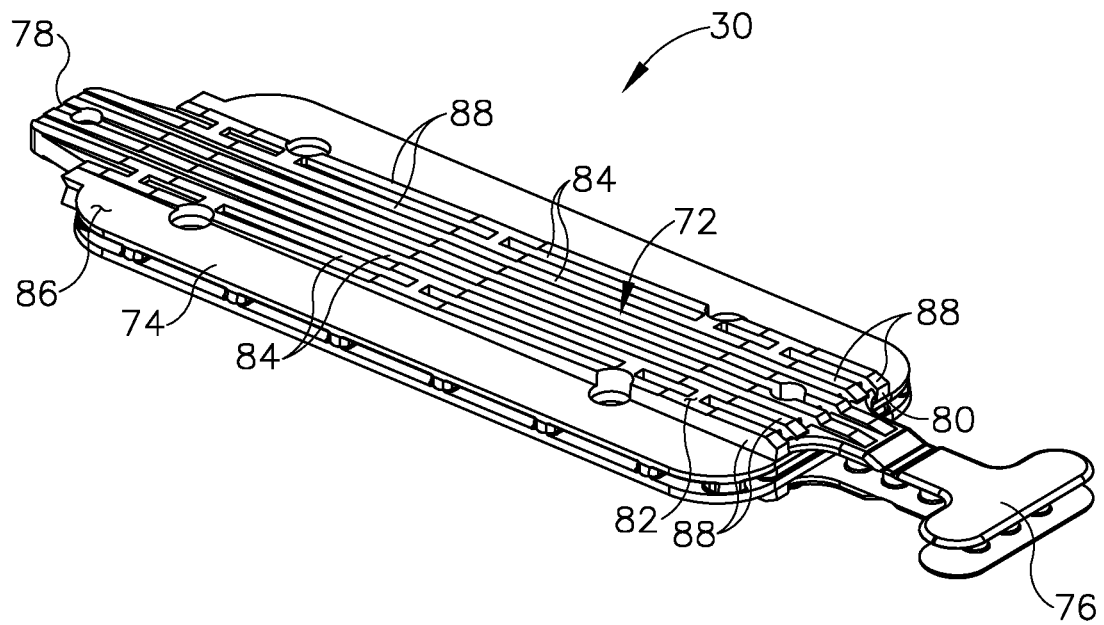
FIG. 5 depicts a rear perspective view of the platform of FIG. 2.

With respect to FIGS. 4-5, a resilient proximal end (78) pad (72) has a proximal end stiffness and a proximal transverse depth, whereas a resilient distal end (80) of pad (72) has a distal end stiffness and a distal transverse depth. In the present example, proximal end stiffness is generally greater than the distal end stiffness such that initial compression of distal end (80) requires less compressive force than compression of proximal end (78). Of course, further compression of distal end (80) relative to proximal end (78) may result in distal end stiffness increasing to or even exceeding proximal end stiffness so long as the lesser stiffness of distal end (80) is included therein for accommodating the over-cambered orientation of end effector (212) (see FIG. 14A).

In addition, distal transverse depth is greater than proximal transverse depth. Thereby, the greater distal transverse depth effectively props up buttress assembly (12) (see FIG. 1) for improved engagement with end effector (212) (see FIG. 10A) in the under-camber orientation, but the decreased distal end stiffness allows for greater compression to accommodate end effector (212) (see FIG. 10A) in the over-camber orientation. Pad (72) of the present example is wedge-shaped having opposing ramp surfaces (82) continuously tapering together from the distal end (80) to the proximal end (78) for accommodating parallel-camber, over-camber, and under-camber orientations along the entire longitudinal length of pad (72). In some examples, depths and stiffnesses along pad (72) are configured to receive a full range of over-camber to under-camber orientations based on determined manufacturing tolerances of end effector (11) (see FIG. 10A).

Figure 6:
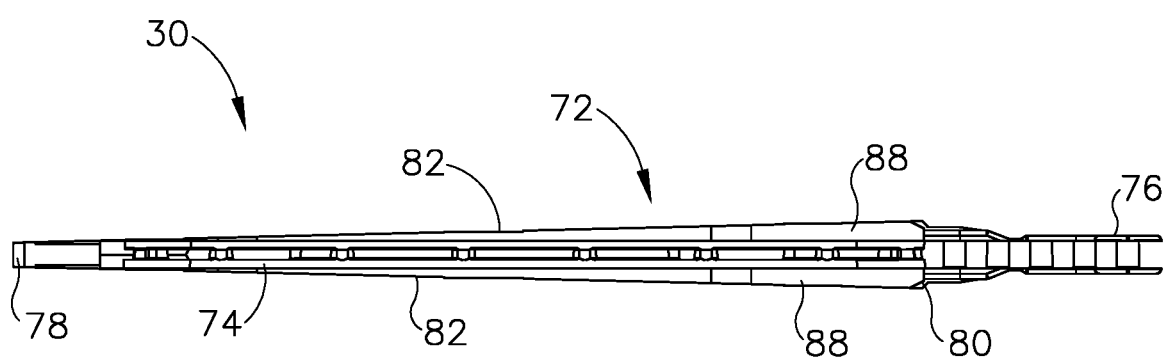
FIG. 6 depicts an elevational side view of the platform of FIG. 2.

Pad (72) shown in FIGS. 4-6 is unitarily formed of a resilient material having a consistent stiffness throughout. Such longitudinally varying stiffness discussed above is thus generated by forming a plurality of reliefs, such as channels (84), in at least the distal end (80) to reduce the distal end stiffness relative to the proximal end stiffness. In the present example, channels (84), such as five channels (84) are equally spaced laterally apart from each other and longitudinally extend from distal end (80) to proximal end (78). Channels (84) further transversely extend to a base surface (86) common to securements (74, 77) and proximal end (78) to define varying channel depths in the longitudinal direction along pad (72). More particularly, upper channels (84) extend transversely downward from upper ramp surface (82) to upper base surface (86), whereas lower channels (84) extend transversely upward from lower ramp surface (82) to lower base surface (86). In turn, a plurality of ribs (88) are defined between channels (84) and similarly extend from ramp surfaces (82) to base surfaces (86) to support buttress assemblies (12) (see FIG. 1) and have varying stiffness from the proximal end (78) to the distal end (80) on each opposing side of pad (72).

ii. Exemplary Restraint Features for Retention of Buttress Assemblies on Varying Stiffness Platform FIGS. 2 and 7-10 show restraint features, such as left and right actuator sleds (52, 54) discussed briefly above for releasably securing buttress assemblies (12) to platform (30) in the restraint position. Each of left and right actuator sleds (52, 54) has arms (55a, 55b, 55c) configured to accommodate varying transverse depths along the longitudinal length of pad (72). More particularly, arms (55a, 55b, 55c) include a distal arm (55a), an intermediate arm (55b), and a proximal arm (55c) spaced longitudinally apart from each other and extending laterally inward toward platform (30). Each distal arm (55a), intermediate arm (55b), and proximal arm (55c) of left or right actuator sled (52, 54) transversely extends toward platform (30) such that each of distal arm (55a), intermediate arm (55b), and proximal arm (55c) is offset from the other arms (55a, 55b, 55c) in the transverse direction. Thereby, distal arm (55a), intermediate arm (55b), and proximal arm (55c) are transversely spaced from the ramp surface (82) to trace the contour of the ramp surface (82).

Figure 7:
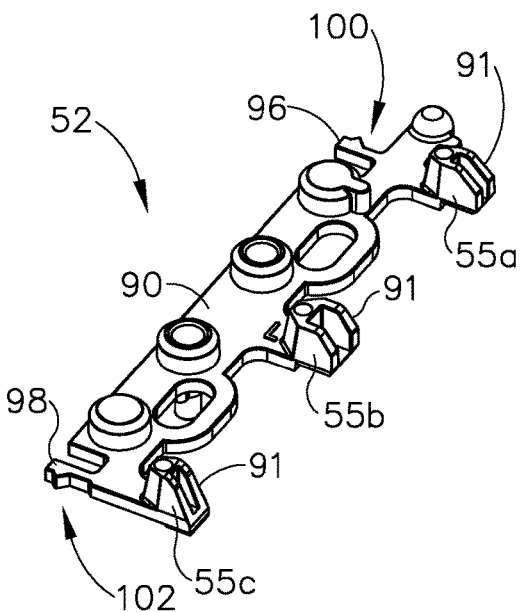
FIG. 7 depicts a top perspective view of a left actuator sled of the buttress applier cartridge assembly of FIG. 2.
Figure 8:
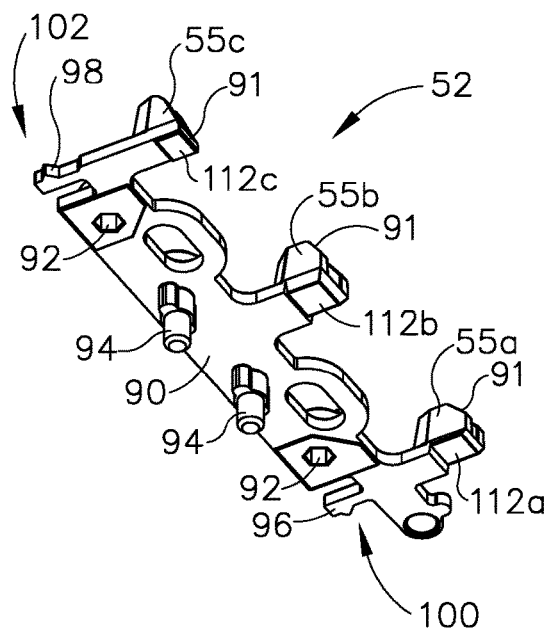
FIG. 8 depicts a bottom perspective view of the left actuator sled of FIG. 7.

With respect to FIGS. 7-8, upper left actuator sled (52) has a longitudinally extending upper left sled body (90) with distal, intermediate, and proximal arms (55a, 55b, 55c) laterally extending inward toward the right. Each arm (55a, 55b, 55c) of left actuator sled (52) has a cam surface (91) configured to receive end effector (212) (see FIG. 14A) thereagainst to urge left actuator sled (52) toward the release position. In addition, a pair of outer dowel holes (92) open downward and are respectively positioned on distal and proximal end portions of upper left sled body (90). A pair of inner dowels (94) extend downward from left sled body (90) between outer dowel holes (92) and in longitudinal alignment with outer dowel holes (92). In order to arrest movement of upper left actuator sled (52) in the restraint and release positions, a distal cantilever catch (96) laterally extends to the left from the distal portion of upper left sled body (90), and a proximal cantilever catch (96) laterally extends to the left from the proximal portion of upper left sled body (90). Distal and proximal cantilever catches (96, 98) are respectively portions of distal and proximal detent couplings (100, 102) discussed below in greater detail.

Figure 9:
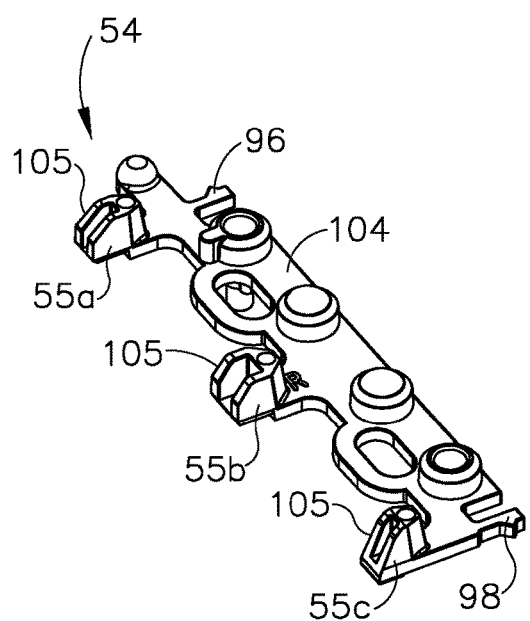
FIG. 9 depicts a top perspective view of a right actuator sled of the buttress applier cartridge assembly of FIG. 2.
Figure 10:
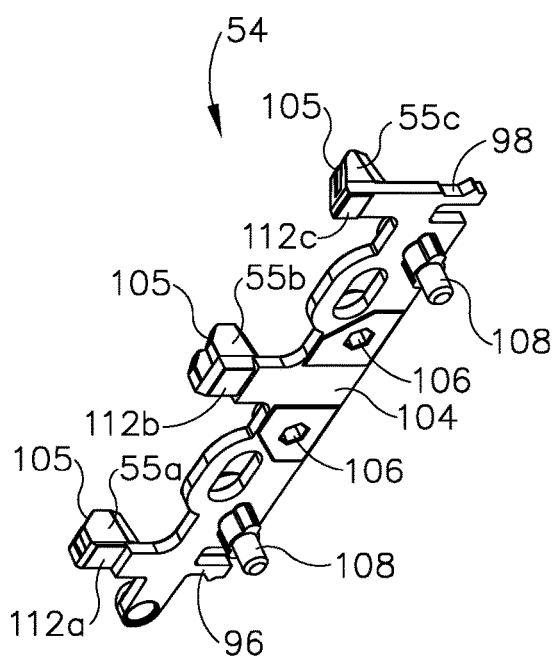
FIG. 10 depicts a bottom perspective view of the right actuator sled of FIG. 9.

With respect to FIGS. 9-10, upper right actuator sled (54) has a longitudinally extending upper right sled body (104) with distal, intermediate, and proximal arms (55a, 55b, 55c) laterally extending inward toward the left. Each arm (55a, 55b, 55c) of right actuator sled (54) has a cam surface (105) configured to receive end effector (212) (see FIG. 14A) thereagainst to urge left actuator sled (52) toward the release position. In addition, a pair of inner dowel holes (106) open downward and are positioned on upper right sled body (104). A pair of outer dowels (108) extend downward from right sled body (104) and are respectively positioned on distal and proximal end portion of upper right sled body (104) in longitudinal alignment with inner dowel holes (106). In order to arrest movement of upper right actuator sled (54) in the restraint and release positions, another distal cantilever catch (96) laterally extends to the right from the distal portion of upper right sled body (104), and another proximal cantilever catch (96) laterally extends to the right from the proximal portion of upper right sled body (104). Again, distal and proximal cantilever catches (96, 98) are respectively portions of distal and proximal detent couplings (100, 102) discussed below in greater detail.

FIG. 2 and FIGS. 11-12 show upper right and left actuator sleds (52, 54) as discussed above in detail as well as lower right and left actuator sleds (52, 54). As briefly discussed above, the description of upper right and left actuator sleds (52, 54) similarly applies to lower right and left actuator sleds (52, 54) with like features having like numbers, but with reversed transverse directions (e.g. lower, upward, etc.). To this end, upper left actuator sled (52) and lower right actuator sled (54) connect together as outer dowels (108) snap into outer dowel holes (92) and inner dowels (94) snap into inner dowel holes (106) with chassis (36) positioned therebetween. Upper right actuator sled (54) and lower left actuator sled (52) similarly connect together as outer dowels (108) snap into outer dowel holes (92) and inner dowels (94) snap into inner dowel holes (106) with chassis (36) positioned therebetween. Each of inner and outer dowels (94, 108) extend through sled clearance holes (70) to slidably connect left and right actuator sleds (52, 54) to chassis (36).

FIG. 12 shows one example of a pair of distal arms (55a), a pair of intermediate arms (55b), and a pair of proximal arms (55c) respectively having platform (30) positioned therebetween and tracing opposing ramp surfaces (82). A central plane (110) is shown in FIG. 12 bisecting upper and lower portions of buttress applier cartridge (16) through a central core of platform (30). Distal arm (55a) has a distal retention surface (112a) transversely offset from central plane (110) a relatively greater distance, intermediate arm (55b) has an intermediate retention surface (112b) transversely offset from central plane (110) a relatively intermediate distance, and proximal arm (55c) has a proximal retention surface (112c) transversely offset from central plane (110) a relatively lesser distance. Thereby, greater, intermediate, and lesser distances of distal, intermediate, and proximal retention surfaces (112a, 112b, 112c) trace ramp surfaces (82) tapering from distal end (80) of pad (72) to proximal end (78) of pad (72). Thus, distal, intermediate, and proximal retention surfaces (112a, 112b, 112c) are offset in the transverse direction from each other and from central plane (110). In the present example, each of distal arm (55a), intermediate arm (55b), and proximal arm (55c) are transversely spaced from the ramp surface (82) an equal transverse dimension such that arms (55a, 55b, 55c) equally trace ramp surfaces (82) tapering from distal end (80) of pad (72) to proximal end (78) of pad (72).

Figure 13A:
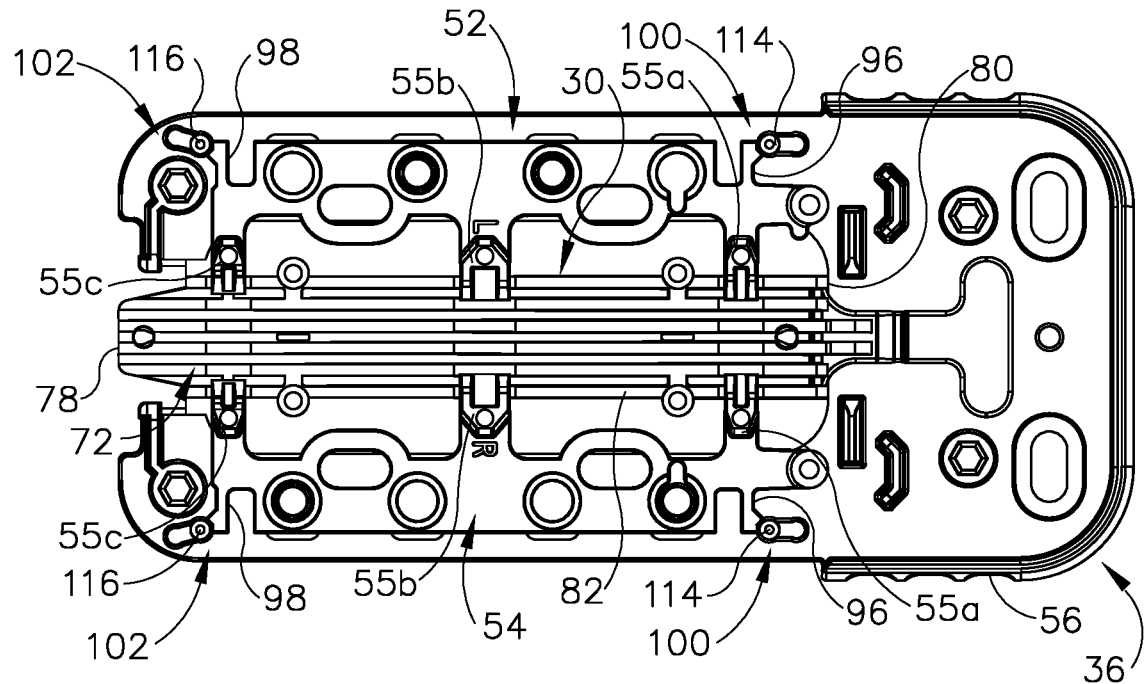
FIG. 13A depicts a top view of the chassis, the platform, and the actuator sleds of FIG. 11 in a restraint position.
Figure 13B:
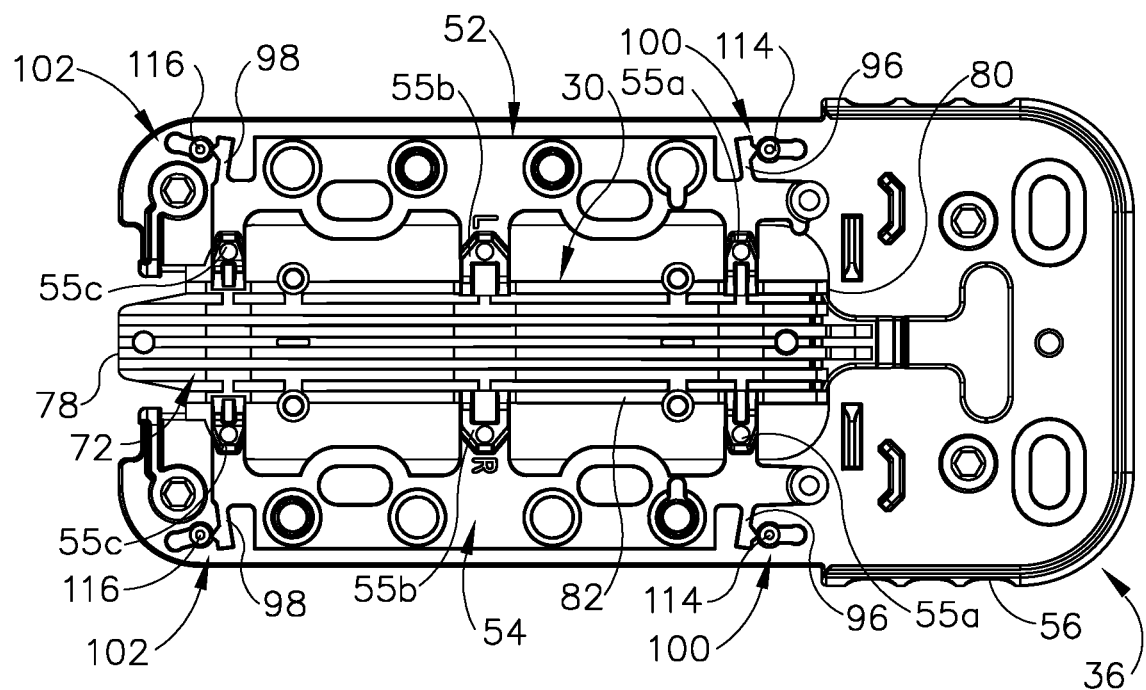
FIG. 13B depicts the top view of the chassis, the platform, and the actuator sleds similar to FIG. 13A, but showing the actuator sleds being directed from the restraint position toward a release position.
Figure 13C:
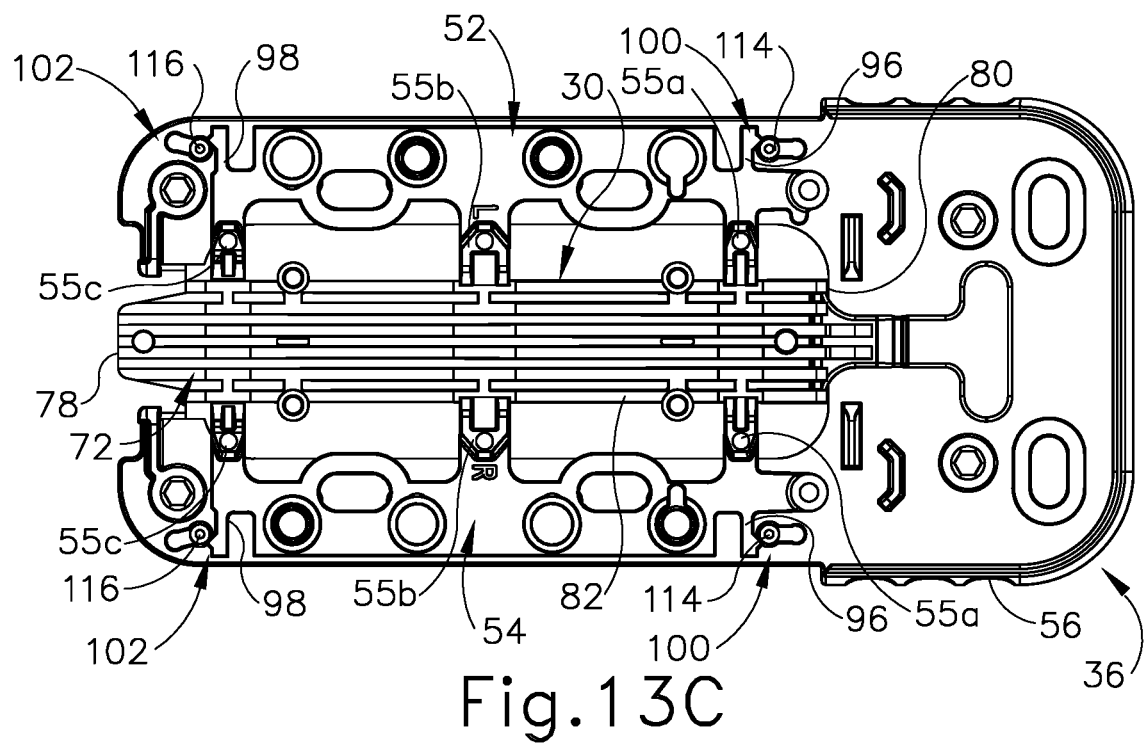
FIG. 13C depicts the top view of the chassis, the platform, and the actuator sleds similar to FIG. 13B, but showing the actuator sleds in the release position.

As shown in FIGS. 13A-13C, left and right actuator sleds (52, 54) are respectively urged outward from the restraint position to the release position away from platform to disengage arms (55a, 55b, 55c) from buttress assemblies (12) (see FIG. 1) on platform (30) as discussed herein. More particularly, distal and proximal detent couplings (100, 102) releasably connected left and right actuator sleds (52, 54) to chassis (36) to arrest movement of left and right actuator sleds (52, 54) in the restraint position and the release position. Distal and proximal detent couplings (100, 102) include distal and proximal cantilever catches (96, 98) extending from each of left and right actuator sleds (52, 54) as discussed briefly above. In addition, distal and proximal detent couplings (100, 102) respectively further include distal and proximal ground cams (114, 116) extending from chassis (36) in respective engagement with distal and proximal cantilever catches (96, 98).

In the restraint position shown in FIG. 13A, each distal cantilever catch (96) is respectively engaged with each distal ground cam (114), and each proximal cantilever catch (98) is respectively engaged with each proximal ground cam (116) to urge left and right actuator sleds (52, 54) inward toward the restraint position. Directing left and right actuator sleds (52, 54) outward from the restraint position toward the release position as shown in FIG. 13B resiliently deflects distal and proximal cantilever catches (96, 98) as distal and proximal cantilever catches (96, 98) follow distal and proximal ground cams (114, 116). As distal and proximal cantilever catches (96, 98) pass around distal and proximal ground cams (114, 116), distal and proximal cantilever catches (96, 98) reach a tipping point where distal and proximal cantilever catches (96, 98) urge left and right actuator sleds (52, 54) to the release position shown in FIG. 13C. In the release position, each distal cantilever catch (96) is respectively engaged with each distal ground cam (114), and each proximal cantilever catch (98) is respectively engaged with each proximal ground cam (116) to urge left and right actuator sleds (52, 54) outward toward the release position. Thereby, distal and proximal detent couplings (100, 102) effectively hold left and right actuator sleds (52, 54) in the release position to inhibit arms (55a, 55b, 55c) from inadvertently returning inward and catching buttress assembly (12) (see FIG. 16) upon removal of end effector (212) (see FIG. 16) as discussed below in greater detail.

C. Exemplary Adhesion of Buttress to Surgical Stapler and Cutting of Buttress Assembly with Tissue As noted above and discussed below in greater detail with respect to FIG. 14A, upper and lower buttress assemblies (12) include upper and lower adhesive layers (42) (or other form of adhesive material) to adhere respective buttresses (14) to an underside (216) of anvil (218) and deck (220) of staple cartridge (222). Such adhesive may provide proper positioning of buttress (14) before and during actuation of end effector (212); then allow buttress (14) to separate from end effector (212) after end effector (212) has been actuated, without causing damage to buttress (14) that is substantial enough to compromise the proper subsequent functioning of buttress (14).

Figure 14B:
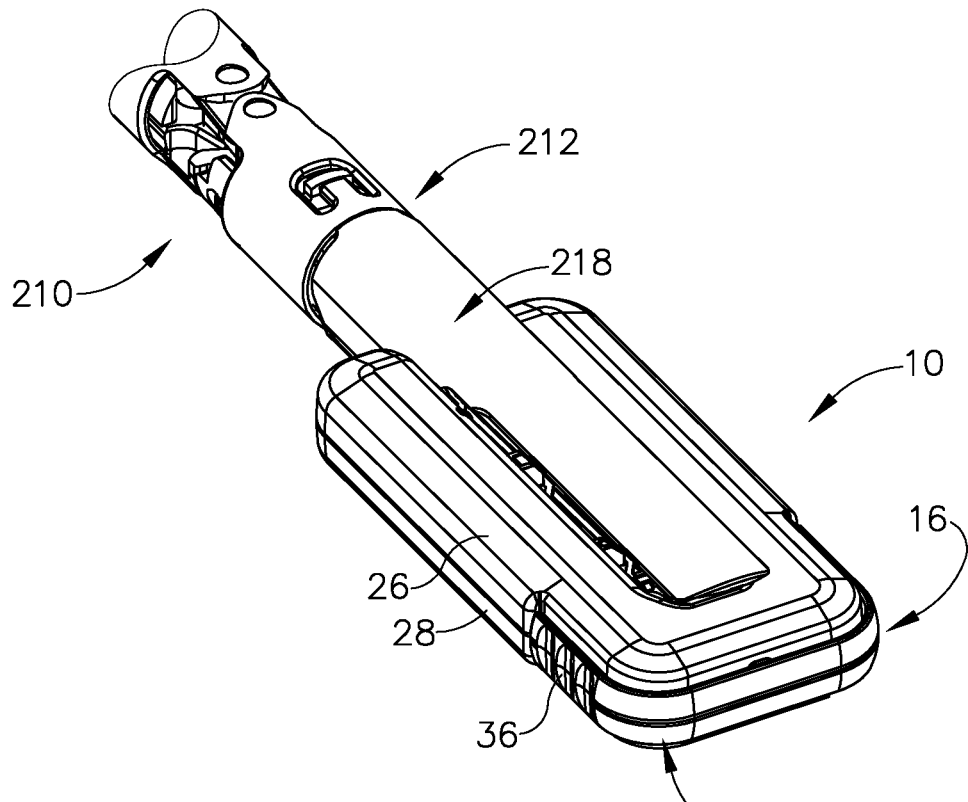
FIG. 14B depicts the perspective view of the end effector similar to FIG. 14A, but showing the buttress applier cartridge assembly of FIG. 1 positioned between the upper and lower jaws in a closed position.

To use buttress applier cartridge (16) to load end effector (212), the operator would first position buttress applier cartridge (16) and end effector (212) such that end effector (212) is aligned with open end (18) of buttress applier cartridge (16) as shown in FIG. 14A. The operator would then advance end effector (212) distally (and/or retract buttress applier cartridge (16) proximally) to position platform (30) and buttress assemblies (12) between anvil (218) and staple cartridge (222). In order to load buttress assemblies (12) on end effector (212), the operator simply closes end effector (212) by pivoting anvil (218) toward staple cartridge (222) to reach the state shown in FIG. 14B.

Figure 15:
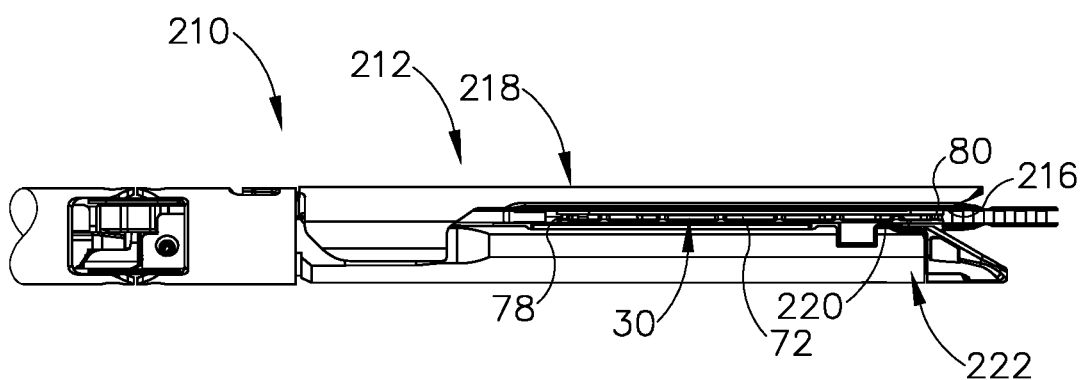
FIG. 15 depicts a side sectional view of the end effector and the platform of the buttress applier cartridge of FIG. 14B in an exemplary parallel-camber orientation, but with various features hidden for greater clarity.
Figure 16:
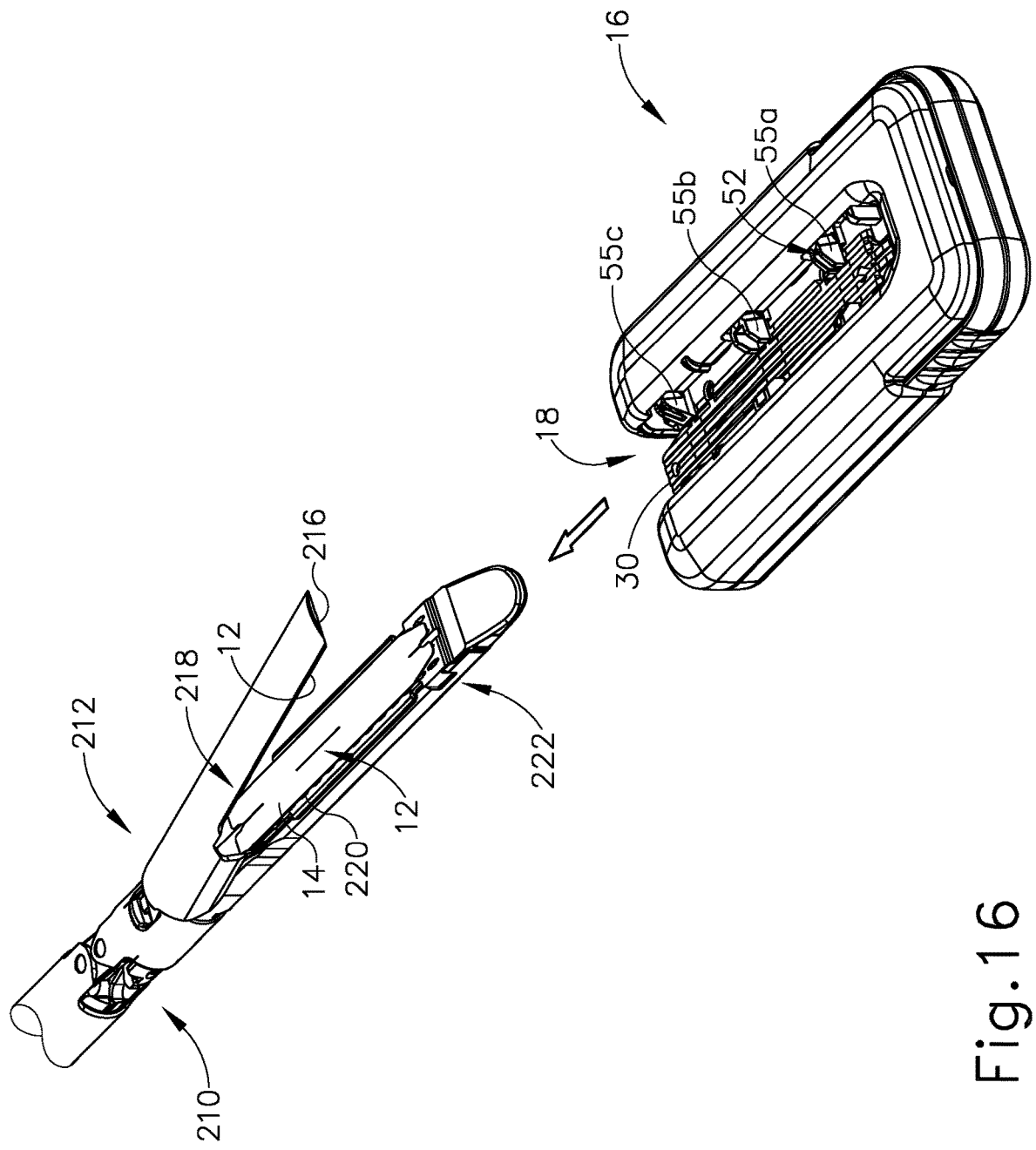
FIG. 16 depicts a perspective view of the end effector similar to FIG. 14B, but showing the buttress assemblies respectively secured to the upper and lower jaws in the open position and the buttress applier cartridge removed therefrom.

As shown, closure of end effector (212) to the parallel-camber orientation results in anvil (218) and staple cartridge (222) bearing against actuator sleds (32), thereby urging arms (34) to unlock buttress assemblies (12) from buttress applier cartridge (16). Adhesive layers (42) of upper and lower buttress assemblies (12) are sufficiently compressed against anvil (218) and deck (220) to retain upper and lower buttress assemblies (12) to end effector (212) for stapling tissue. Pad (72) accommodates the parallel-camber orientation shown in FIG. 15 by providing reaction forces of at least the predetermined minimum force for adhesion along the longitudinal length of buttress assemblies (12). Upon depositing buttress assemblies (12) onto anvil (218) and staple cartridge (222), the operator removes buttress applier cartridge (16) from end effector (212) as shown in FIG. 16.

Figure 17:
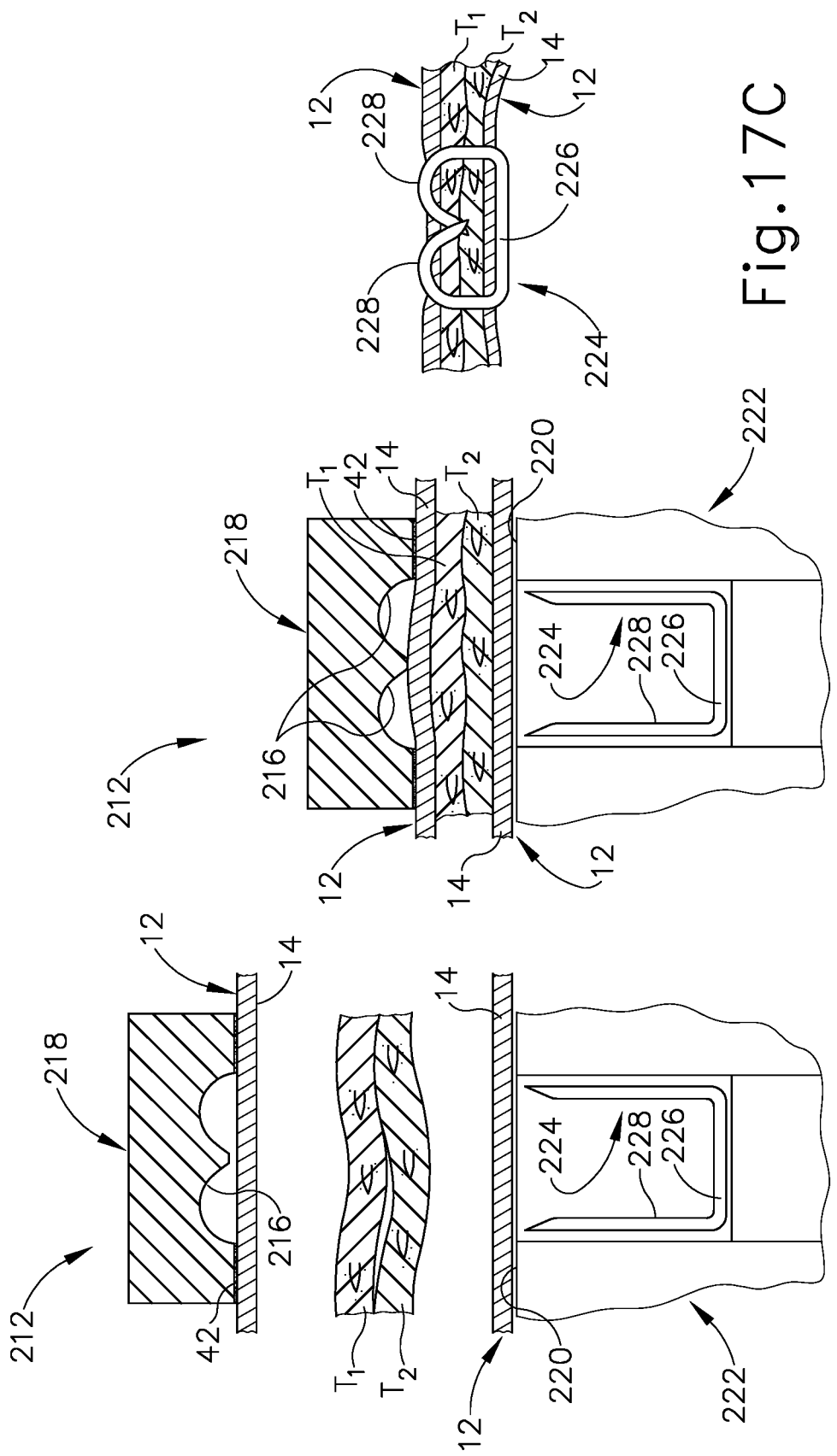
FIG. 17A depicts a sectional side view of a portion of the end effector of FIG. 14B with the buttress assemblies of FIG. 1 applied to the end effector and tissue positioned between the buttress assemblies with the upper and lower jaws in the open position.
FIG. 17B depicts the sectional side view of the portion of the end effector and the buttress assemblies similar to FIG. 17A, but showing the upper and lower jaws in the closed position.
FIG. 17C depicts the sectional side view of the buttress assemblies similar to FIG. 17B, but showing the buttress assemblies secured to the tissue with a staple formed in the tissue.

To this end, FIGS. 17A-17C show a sequence where end effector (212) loaded with buttress assemblies (12) is actuated to drive a plurality of staples (224) through two apposed layers of tissue ($T_1$, $T_2$), with buttress assemblies (12) being secured to the same layers of tissue ($T_1$, $T_2$) by staples (224). In particular, FIG. 17A shows layers of tissue ($T_1$, $T_2$) positioned between anvil (218) and staple cartridge (222), with anvil (218) in the open position. Upper buttress assembly (12) is adhered to the underside (216) of anvil (218) via adhesive layer (42); while lower buttress assembly (12) is adhered to deck (220) of staple cartridge (222) via adhesive layer (42). Layers of tissue ($T_1$, $T_2$) are thus interposed between upper and lower buttress assemblies (12). Next, a trigger (not shown) is pivoted to drive anvil (218) to the closed position as shown in FIG. 17B. At this stage, layers of tissue (T₁, T₂) are compressed between anvil (218) and staple cartridge (222), with upper and lower buttress assemblies (12) engaging opposite surfaces of tissue layers (T₁, T₂). End effector (212) is then actuated as described above, driving staple (224) through upper and lower buttress assemblies (12) and layers of tissue (T₁, T₂). As shown in FIG. 17C, a crown (226) of driven staple (224) captures and retains lower buttress assembly (12) against layer of tissue (T₂). Deformed legs (228) of staple (224) capture and retain upper buttress assembly (12) against layer of tissue (T₁).

It should be understood that a series of staples (224) will similarly capture and retain upper and lower buttress assemblies (12) against layers of tissue (T₁, T₂), thereby securing upper and lower buttress assemblies (12) to tissue (T₁, T₂). In one example, knife (not shown) cuts through a centerline of buttress assemblies (12), separating buttress assemblies (12) into a corresponding pair of sections, such that each section remains secured to a respective severed region of tissue (T₁, T₂) as shown in FIG. 18.

Figure 18:
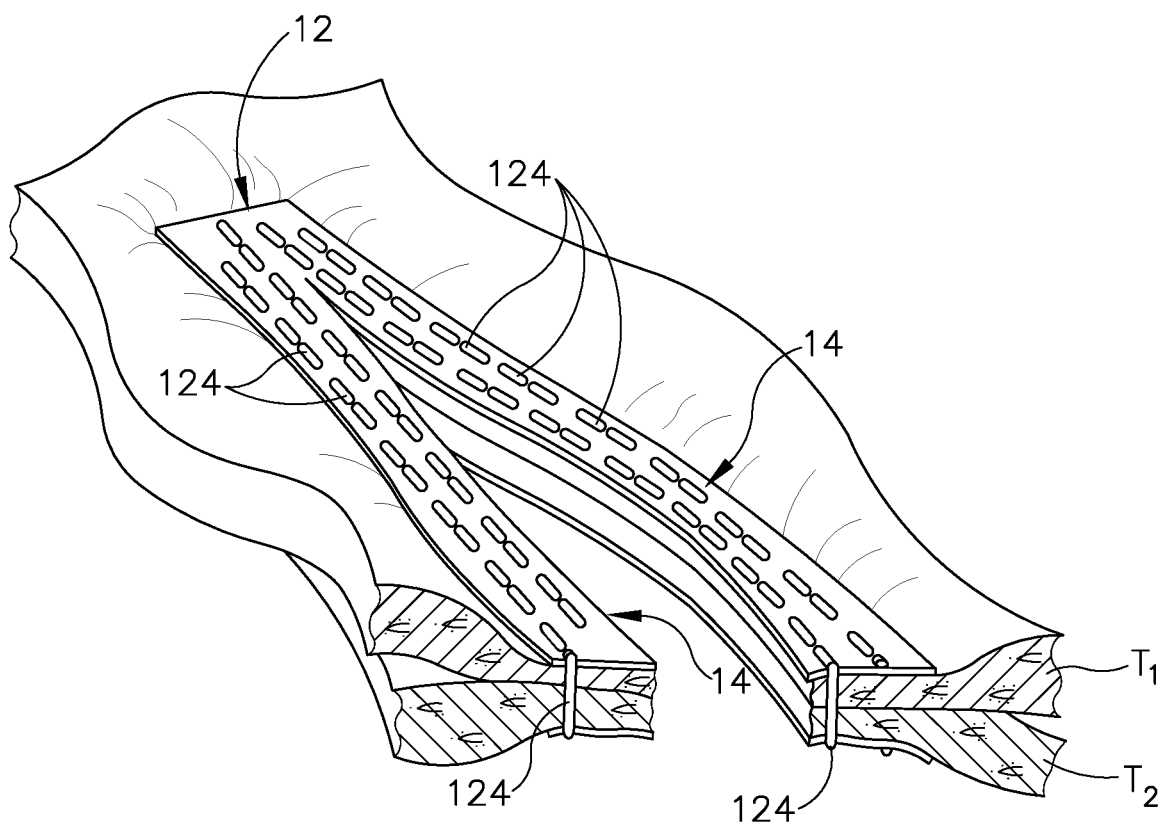
FIG. 18 depicts a perspective view of staples and the buttress assembly of FIG. 17C having been secured to the tissue by the end effector and cut by a knife.

With respect to FIG. 18, as end effector (212) (see FIG. 16) is pulled away from tissue (T₁, T₂) after deploying staples (224) and upper and lower buttress assemblies (12), upper and lower buttress assemblies (12) disengage end effector (212), such that upper and lower buttress assemblies (12) remain secured to tissue (T₁, T₂) with staples (224). Buttressed tissue (T₁, T₂) thus provides structural reinforcement to the lines of staples (224). In addition to the foregoing, it should also be understood that any of the various buttress assemblies described herein may be further constructed and operable in accordance with at least some of the teachings of U.S. Pat. Pub. No. 2016/0278774, entitled "Method of Applying a Buttress to a Surgical Stapler," published Sep. 29, 2016, issued as U.S. Pat. No. 10,349,939 on Jul. 16, 2019, the disclosure of which is incorporated by reference herein.

FIGS. 19-20 show pad (72) accommodating alternative camber orientations of end effector (212), such as the over-camber orientation and the under-camber orientation. With respect to FIG. 19, closure of end effector (212) to the over-camber orientation results in anvil (218) and staple cartridge (222) unlocking buttress assemblies (12) from buttress applier cartridge (16) as discussed above. Adhesive layers (42) of upper and lower buttress assemblies (12) are sufficiently compressed against anvil (218) and deck (220) to retain upper and lower buttress assemblies (12) to end effector (212) for stapling tissue. Pad (72) accommodates the over-camber orientation by providing reaction forces of at least the predetermined minimum force for adhesion along the longitudinal length of buttress assemblies (12).

Similarly, FIG. 20 shows closure of end effector (212) to the under-camber orientation resulting in anvil (218) and staple cartridge (222) unlocking buttress assemblies (12) from buttress applier cartridge (16) as discussed above. Adhesive layers (42) of upper and lower buttress assemblies (12) are sufficiently compressed against anvil (218) and deck (220) to retain upper and lower buttress assemblies (12) to end effector (212) for stapling tissue. Pad (72) accommodates the under-camber orientation by providing reaction forces of at least the predetermined minimum force for adhesion along the longitudinal length of buttress assemblies (12).

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A buttress applier cartridge assembly, comprising: (a) a first buttress assembly, including: (i) a first buttress configured to be received against tissue and support a staple formed therein, and (ii) a first adhesive layer on the first buttress configured to releasably adhere the first buttress against a first portion of an end effector of a surgical stapler upon engaging the first adhesive layer against the end effector with at least a predetermined minimum force; and (b) a buttress applier cartridge, including: (i) a housing defining a first gap extending in a longitudinal direction therealong such that the first gap is configured to receive the first portion of the end effector, and (ii) a platform extending longitudinally from a proximal platform portion to a distal platform portion and operatively connected to the housing, wherein the platform is exposed in a transverse direction adjacent to the first gap and the proximal and distal platform portions respectively have a proximal stiffness and a different, distal stiffness in the transverse direction, wherein the proximal and distal platform portions support the first buttress assembly thereon and are configured to deform with the proximal and distal stiffnesses thereby providing reactionary forces of at least the predetermined minimum force while receiving the end effector for accommodating various camber orientations of the end effector.

Example 2

The buttress applier cartridge assembly of Example 1, further comprising: (a) a second buttress assembly, including: (i) a second buttress configured to be received against tissue and support the staple formed therein, and (ii) a second adhesive layer on the second buttress configured to releasably adhere the second buttress against a second portion of the end effector upon engaging the second adhesive layer against the end effector with at least the predetermined minimum force; and (b) the buttress applier cartridge, further including: (i) the housing defining a second gap extending in the longitudinal direction therealong such that the second gap is configured to receive the second portion of the end effector, and (ii) the platform exposed in the transverse direction between the first and second gaps, wherein the proximal and distal platform portions support the first and second buttress assemblies on opposing transverse sides thereof and are configured to deform with the proximal and distal stiffnesses thereby providing reactionary forces of at least the predetermined minimum force while receiving the end effector for accommodating various camber orientations of the first portion of the end effector relative to the second portion of the end effector.

Example 3

The buttress applier cartridge assembly of any one or more of Examples 1 through 2, wherein the proximal platform portion has a proximal transverse depth, wherein the distal platform portion has a distal transverse depth, and wherein the proximal transverse depth is less than the distal transverse depth.

Example 4

The buttress applier cartridge assembly of any one or more of Examples 1 through 3, wherein the platform continuously tapers from the distal platform portion toward the proximal platform portion.

Example 5

The buttress applier cartridge assembly of any one or more of Examples 1 through 4, wherein the platform is wedge-shaped.

Example 6

The buttress applier cartridge assembly of any one or more of Examples 1 through 5, wherein the platform includes a platform pad and a plurality of reliefs in at least one of the proximal and distal platform portions, wherein the plurality of reliefs are configured to generate the differing proximal and distal stiffnesses in the platform.

Example 7

The buttress applier cartridge assembly of Example 6, wherein the plurality of reliefs include a plurality of channels, wherein the plurality of channels extend transversely into the platform pad and longitudinally along the proximal and distal platform portions.

Example 8

The buttress applier cartridge assembly of Example 7, wherein the platform pad includes a plurality of ribs extending longitudinally along the proximal and distal platform portions such that the plurality of channels are respectively defined between the plurality of ribs.

Example 9

The buttress applier cartridge assembly of Example 8, wherein the proximal platform portion has a proximal transverse depth, wherein the proximal platform portion has a distal transverse depth, and wherein the proximal transverse depth is less than the distal transverse depth.

Example 10

The buttress applier cartridge assembly of Example 9, wherein the platform pad continuously tapers from the distal platform portion toward the proximal platform portion.

Example 11

The buttress applier cartridge assembly of Example 10, wherein the platform pad is wedge-shaped.

Example 12

The buttress applier cartridge assembly of any one or more of Examples 6 through 11, wherein the platform pad is unitarily formed from a resilient material.

Example 13

The buttress applier cartridge assembly of any one or more of Examples 1 through 12, further comprising a chassis connected to the housing and having a rigid web portion defining a plurality of holes, and wherein the rigid web portion extends laterally through the platform thereby securing the rigid web portion of the chassis to the platform.

Example 14

The buttress applier cartridge assembly of any one or more of Examples 1 through 13, further comprising: (a) an actuator sled operatively connected to the housing and configured to selectively move relative to the housing from a restraint position to a release position, wherein the actuator sled in the restraint position is configured to capture the first buttress assembly to the platform, and wherein actuator sled in the release position is configured to release the first buttress assembly from the platform for removing the first buttress assembly therefrom; and (b) a detent coupling operatively connected to the actuator sled and configured arrest movement of the actuator sled in the restraint position when the actuator sled is in the restraint position, and wherein the detent coupling is further configured to arrest movement of the actuator sled in the release position when the actuator sled is in the release position.

Example 15

The buttress applier cartridge assembly of Example 1, wherein the proximal platform portion has a proximal transverse depth, wherein the distal platform portion has a distal transverse depth, and wherein the proximal transverse depth is different than the distal transverse depth, and wherein the buttress applier cartridge further comprises: (a) an actuator sled operatively connected to the housing and configured to selectively move relative to the housing from a restraint position to a release position, wherein the actuator sled in the restraint position is configured to capture the first buttress assembly to the platform, and wherein actuator sled in the release position is configured to release the first buttress assembly from the platform for removing the first buttress assembly therefrom, wherein the actuator sled further includes: (i) a distal arm extending laterally toward the first buttress assembly and longitudinally aligned with the distal platform portion, and (ii) a proximal arm extending laterally toward the first buttress assembly and longitudinally aligned with the proximal platform portion, wherein the distal arm is transversely offset relative to the proximal arm such that the distal and proximal arms respectively engage the first buttress assembly at the distal and proximal platform portions in the restraint position.

Example 16

A buttress applier cartridge assembly, comprising: (a) a first buttress assembly, including: (i) a first buttress configured to be received against tissue and support a staple formed therein, and (ii) a first adhesive layer on the first buttress configured to releasably adhere the first buttress against a first portion of an end effector of a surgical stapler upon engaging the first adhesive layer against the end effector with at least a predetermined minimum force; (b) a buttress applier cartridge, including: (i) a housing defining a first gap extending in a longitudinal direction therealong such that the first gap is configured to receive the first portion of the end effector, and (ii) a platform extending longitudinally from a proximal platform portion to a distal platform portion and operatively connected to the housing, wherein the platform is exposed in a transverse direction adjacent to the first gap, wherein the proximal and distal platform portions support the first buttress assembly thereon; (c) a first actuator sled operatively connected to the housing and configured to selectively move relative to the housing from a first restraint position to a first release position, wherein the first actuator sled in the first restraint position is configured to capture the first buttress assembly to the platform, and wherein actuator sled in the first release position is configured to release the first buttress assembly from the platform for removing the first buttress assembly therefrom; and (d) a first detent coupling operatively connected to the first actuator sled and configured arrest movement of the first actuator sled in the restraint position when the first actuator sled is in the first restraint position, and wherein the first detent coupling is further configured to arrest movement of the first actuator sled in the first release position when the first actuator sled is in the first release position.

Example 17

The buttress applier cartridge assembly of Example 16, further comprising: (a) a second buttress assembly, including: (i) a second buttress configured to be received against tissue and support the staple formed therein, and (ii) a second adhesive layer on the second buttress configured to releasably adhere the second buttress against a second portion of the end effector upon engaging the second adhesive layer against the end effector with at least the predetermined minimum force; and (b) the buttress applier cartridge, further including: (i) the housing defining a second gap extending in the longitudinal direction therealong such that the second gap is configured to receive the second portion of the end effector, and (ii) the platform exposed in the transverse direction between the first and second gaps, wherein the proximal and distal platform portions support the first and second buttress assemblies on opposing transverse sides thereof.

Example 18

The buttress applier cartridge assembly of any one or more of Examples 16 through 17, further comprising: (a) a second actuator sled operatively connected to the housing and configured to selectively move relative to the housing from a second restraint position to a second release position, wherein the second actuator sled in the second restraint position is configured to capture the first buttress assembly to the platform, and wherein actuator sled in the second release position is configured to release the first buttress assembly from the platform for removing the first buttress assembly therefrom; and (b) a second detent coupling operatively connected to the second actuator sled and configured arrest movement of the second actuator sled in the restraint position when the second actuator sled is in the second restraint position, and wherein the second detent coupling is further configured to arrest movement of the second actuator sled in the second release position when the first actuator sled is in the second release position.

Example 19

The buttress applier cartridge assembly of any one or more of Examples 16 through 18, wherein the proximal platform portion has a proximal transverse depth, wherein the distal platform portion has a distal transverse depth, and wherein the proximal transverse depth is different than the distal transverse depth, and wherein the first actuator sled further includes a distal arm and a proximal arm, wherein the distal arm extends laterally toward the first buttress assembly and longitudinally aligned with the distal platform portion, wherein the proximal arm extends laterally toward the first buttress assembly and is longitudinally aligned with the proximal platform portion, and wherein the distal arm is transversely offset relative to the proximal arm such that the distal and proximal arms respectively engage the first buttress assembly at the distal and proximal platform portions in the restraint position.

Example 20

A buttress applier cartridge assembly, comprising: (a) a buttress assembly, including: (i) a buttress configured to be received against tissue and support a staple formed therein, and (ii) an adhesive layer on the buttress configured to releasably adhere the buttress against a portion of an end effector of a surgical stapler upon engaging the adhesive layer against the end effector with at least a predetermined minimum force; (b) a buttress applier cartridge, including: (i) a housing defining a gap extending in a longitudinal direction therealong such that the gap is configured to receive the portion of the end effector, and (ii) a platform extending longitudinally from a proximal platform portion to a distal platform portion and operatively connected to the housing, wherein the platform is exposed in a transverse direction adjacent to the gap and supports the buttress assembly thereon, wherein proximal and distal platform portions respectively have a proximal transverse depth and a distal transverse, wherein the proximal transverse depth is different than the distal transverse depth; and (c) an actuator sled operatively connected to the housing and configured to selectively capture the buttress assembly to the platform in a restraint position, wherein the actuator sled, includes: (i) a distal arm extending laterally toward the buttress assembly and longitudinally aligned with the distal platform portion, and (ii) a proximal arm extending laterally toward the buttress assembly and longitudinally aligned with the proximal platform portion, wherein the distal arm is transversely offset relative to the proximal arm such that the distal and proximal arms respectively engage the buttress assembly at the distal and proximal platform portions in the restraint position.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

In addition to the foregoing, it should also be understood that any of the various buttress assemblies described herein may be further constructed and operable in accordance with at least some of the teachings of U.S. Pat. Pub. No. 2016/0278774, entitled "Method of Applying a Buttress to a Surgical Stapler," published Sep. 29, 2016, issued as U.S. Pat. No. 10,349,939 on Jul. 16, 2019, the disclosure of which is incorporated by reference herein; U.S. Pat. Pub. No. 2017/0049444, entitled "Implantable Layers for a Surgical Instrument," published Feb. 23, 2017, issued as U.S. Pat. No. 10,835,249 on Nov. 17, 2020, the disclosure of which is incorporated by reference herein; U.S. Pat. Pub. No. 2017/0086837, entitled "Compressible Adjunct with Crossing Spacer Fibers," published Mar. 30, 2017, issued as U.S. Pat. No. 10,433,846 on Oct. 8, 2019, the disclosure of which is incorporated by reference herein; and U.S. Pat. Pub. No. 2017/0086842, entitled "Method for Applying an Implantable Layer to a Fastener Cartridge," published Mar. 30, 2017, the disclosure of which is incorporated by reference herein. Furthermore, in addition to the methods described herein, any of the various buttress assemblies described herein may be applied to end effector (212) in accordance with at least some of the teachings of U.S. Provisional Patent App. No. 62/209,041, entitled "Method and Apparatus for Applying a Buttress to End Effector of a Surgical Stapler," filed Aug. 24, 2015, the disclosure of which is incorporated by reference herein; and/or U.S. Pat. Pub. No. 2017/0086842, entitled "Method for Applying an Implantable Layer to a Fastener Cartridge," published Mar. 30, 2017, the disclosure of which is incorporated by reference herein. Various suitable ways in which the teachings herein may be combined with various teachings of the above-cited references will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A buttress applier cartridge assembly, comprising:
 (a) a first buttress assembly, including:
  (i) a first buttress configured to be received against tissue and support a staple formed therein, and
  (ii) a first adhesive layer on the first buttress configured to releasably adhere the first buttress against a first portion of an end effector of a surgical stapler upon engaging the first adhesive layer against the end effector with at least a predetermined minimum force; and
 (b) a buttress applier cartridge, including:
  (i) a housing defining a first gap extending in a longitudinal direction therealong such that the first gap is configured to receive the first portion of the end effector, and
  (ii) a platform extending longitudinally from a proximal platform portion to a distal platform portion and operatively connected to the housing, wherein the platform is exposed in a transverse direction adjacent to the first gap and the proximal and distal platform portions respectively have a proximal stiffness and a different, distal stiffness in the transverse direction, wherein the proximal and distal platform portions support the first buttress assembly thereon and are configured to deform with the proximal and distal stiffnesses thereby providing reactionary forces of at least the predetermined minimum force while receiving the end effector for accommodating various camber orientations of the end effector,
wherein the platform includes a plurality of reliefs in the form of a plurality of channels extending longitudinally along at least one of the proximal or distal platform portions, wherein the channels are configured to generate the differing proximal and distal stiffnesses in the platform, wherein at least one of the channels has a proximal channel depth and a distal channel depth,
wherein the proximal channel depth is different than the distal channel depth.

2. The buttress applier cartridge assembly of claim 1, further comprising:
(a) a second buttress assembly, including:
(i) a second buttress configured to be received against tissue and support the staple formed therein, and
(ii) a second adhesive layer on the second buttress configured to releasably adhere the second buttress against a second portion of the end effector upon engaging the second adhesive layer against the end effector with at least the predetermined minimum force; and
(b) the buttress applier cartridge, further including:
(i) the housing defining a second gap extending in the longitudinal direction therealong such that the second gap is configured to receive the second portion of the end effector, and
(ii) the platform exposed in the transverse direction between the first and second gaps,
wherein the proximal and distal platform portions support the first and second buttress assemblies on opposing transverse sides thereof and are configured to deform with the proximal and distal stiffnesses thereby providing reactionary forces of at least the predetermined minimum force while receiving the end effector for accommodating various camber orientations of the first portion of the end effector relative to the second portion of the end effector.

3. The buttress applier cartridge assembly of claim 1, wherein the proximal platform portion has a proximal transverse depth, wherein the distal platform portion has a distal transverse depth, and wherein the proximal transverse depth is less than the distal transverse depth.

4. The buttress applier cartridge assembly of claim 3, wherein the platform continuously tapers from the distal platform portion toward the proximal platform portion.

5. The buttress applier cartridge assembly of claim 4, wherein the platform is wedge-shaped.

6. The buttress applier cartridge assembly of claim 1, wherein the platform includes a platform pad, wherein the plurality of channels extend transversely into the platform pad and longitudinally along the proximal and distal platform portions.

7. The buttress applier cartridge assembly of claim 6, wherein the platform pad includes a plurality of ribs extending longitudinally along the proximal and distal platform portions such that the plurality of channels are respectively defined between the plurality of ribs.

8. The buttress applier cartridge assembly of claim 7, wherein the proximal platform portion has a proximal transverse depth, wherein the proximal platform portion has a distal transverse depth, and wherein the proximal transverse depth is less than the distal transverse depth.

9. The buttress applier cartridge assembly of claim 8, wherein the platform pad continuously tapers from the distal platform portion toward the proximal platform portion.

10. The buttress applier cartridge assembly of claim 9, wherein the platform pad is wedge-shaped.

11. The buttress applier cartridge assembly of claim 9, wherein the platform pad is unitarily formed from a resilient material.

12. The buttress applier cartridge assembly of claim 1, further comprising a chassis connected to the housing and having a rigid web portion defining a plurality of holes, and wherein the rigid web portion extends laterally through the platform thereby securing the rigid web portion of the chassis to the platform.

13. The buttress applier cartridge assembly of claim 1, further comprising:
(a) an actuator sled operatively connected to the housing and configured to selectively move relative to the housing from a restraint position to a release position, wherein the actuator sled in the restraint position is configured to capture the first buttress assembly to the platform, and wherein actuator sled in the release position is configured to release the first buttress assembly from the platform for removing the first buttress assembly therefrom; and
(b) a detent coupling operatively connected to the actuator sled and configured arrest movement of the actuator sled in the restraint position when the actuator sled is in the restraint position, and wherein the detent coupling is further configured to arrest movement of the actuator sled in the release position when the actuator sled is in the release position.

14. The buttress applier cartridge assembly of claim 1, wherein the proximal platform portion has a proximal transverse depth, wherein the distal platform portion has a distal transverse depth, and wherein the proximal transverse depth is different than the distal transverse depth, and wherein the buttress applier cartridge further comprises:
(a) an actuator sled operatively connected to the housing and configured to selectively move relative to the housing from a restraint position to a release position, wherein the actuator sled in the restraint position is configured to capture the first buttress assembly to the platform, and wherein actuator sled in the release position is configured to release the first buttress assembly from the platform for removing the first buttress assembly therefrom, wherein the actuator sled further includes:
(i) a distal arm extending laterally toward the first buttress assembly and longitudinally aligned with the distal platform portion, and
(ii) a proximal arm extending laterally toward the first buttress assembly and longitudinally aligned with the proximal platform portion,
wherein the distal arm is transversely offset relative to the proximal arm such that the distal and proximal arms respectively engage the first buttress assembly at the distal and proximal platform portions in the restraint position.

15. A buttress applier cartridge assembly, comprising:
(a) a first buttress assembly, including:
(i) a first buttress configured to be received against tissue and support a staple formed therein, and
(ii) a first adhesive layer on the first buttress configured to releasably adhere the first buttress against a first portion of an end effector of a surgical stapler upon engaging the first adhesive layer against the end effector with at least a predetermined minimum force;

(b) a buttress applier cartridge, including:
  (i) a housing defining a first gap extending in a longitudinal direction therealong such that the first gap is configured to receive the first portion of the end effector, and
  (ii) a platform extending longitudinally from a proximal platform portion to a distal platform portion and operatively connected to the housing, wherein the platform is exposed in a transverse direction adjacent to the first gap,
  wherein the proximal and distal platform portions support the first buttress assembly thereon;
(c) a first actuator sled operatively connected to the housing and configured to selectively move laterally relative to the housing and the longitudinal axis from a first restraint position to a first release position, wherein the first actuator sled in the first restraint position is configured to capture the first buttress assembly to the platform, and wherein actuator sled in the first release position is configured to release the first buttress assembly from the platform for removing the first buttress assembly therefrom; and
(d) a first detent coupling extending laterally from the first actuator sled and configured to arrest lateral movement of the first actuator sled when the first actuator sled is in the first restraint position, and wherein the first detent coupling is further configured to arrest lateral movement of the first actuator sled when the first actuator sled is in the first release position.

16. The buttress applier cartridge assembly of claim 15, further comprising:
(a) a second buttress assembly, including:
  (i) a second buttress configured to be received against tissue and support the staple formed therein, and
  (ii) a second adhesive layer on the second buttress configured to releasably adhere the second buttress against a second portion of the end effector upon engaging the second adhesive layer against the end effector with at least the predetermined minimum force; and
(b) the buttress applier cartridge, further including:
  (i) the housing defining a second gap extending in the longitudinal direction therealong such that the second gap is configured to receive the second portion of the end effector, and
  (ii) the platform exposed in the transverse direction between the first and second gaps,
  wherein the proximal and distal platform portions support the first and second buttress assemblies on opposing transverse sides thereof.

17. The buttress applier cartridge assembly of claim 15, further comprising:
(a) a second actuator sled operatively connected to the housing and configured to selectively move relative to the housing from a second restraint position to a second release position, wherein the second actuator sled in the second restraint position is configured to capture the first buttress assembly to the platform, and wherein actuator sled in the second release position is configured to release the first buttress assembly from the platform for removing the first buttress assembly therefrom; and
(b) a second detent coupling operatively connected to the second actuator sled and configured arrest movement of the second actuator sled in the restraint position when the second actuator sled is in the second restraint position, and wherein the second detent coupling is further configured to arrest movement of the second actuator sled in the second release position when the first actuator sled is in the second release position.

18. The buttress applier cartridge assembly of claim 15, wherein the proximal platform portion has a proximal transverse depth, wherein the distal platform portion has a distal transverse depth, and wherein the proximal transverse depth is different than the distal transverse depth, and wherein the first actuator sled further includes a distal arm and a proximal arm, wherein the distal arm extends laterally toward the first buttress assembly and longitudinally aligned with the distal platform portion, wherein the proximal arm extends laterally toward the first buttress assembly and is longitudinally aligned with the proximal platform portion, and wherein the distal arm is transversely offset relative to the proximal arm such that the distal and proximal arms respectively engage the first buttress assembly at the distal and proximal platform portions in the restraint position.

19. A buttress applier cartridge assembly, comprising:
(a) a buttress assembly, including:
  (i) a buttress configured to be received against tissue and support a staple formed therein, and
  (ii) an adhesive layer on the buttress configured to releasably adhere the buttress against a portion of an end effector of a surgical stapler upon engaging the adhesive layer against the end effector with at least a predetermined minimum force;
(b) a buttress applier cartridge extending along a central plane, including:
  (i) a housing defining a gap extending in a longitudinal direction therealong such that the gap is configured to receive the portion of the end effector, and
  (ii) a platform extending longitudinally from a proximal platform portion to a distal platform portion and operatively connected to the housing, wherein the platform is exposed in a transverse direction adjacent to the gap and supports the buttress assembly thereon, wherein the proximal and distal platform portions respectively have a proximal transverse depth and a distal transverse depth, wherein the proximal transverse depth is different than the distal transverse depth; and
(c) an actuator sled operatively connected to the housing and configured to selectively capture the buttress assembly to the platform in a restraint position, wherein the actuator sled, includes:
  (i) a distal arm extending laterally toward the buttress assembly and longitudinally aligned with the distal platform portion, and
  (ii) a proximal arm extending laterally toward the buttress assembly and longitudinally aligned with the proximal platform portion,
  wherein the distal arm is transversely offset a first distance from the central plane and the proximal arm is transversely offset a second distance from the central plane such that the distal and proximal arms respectively engage the buttress assembly at the distal and proximal platform portions in the restraint position.

20. The buttress applier cartridge assembly of claim 1, wherein the buttress applier cartridge further comprises an actuator sled operatively connected to the housing and configured to selectively move relative to the housing from a restraint position to a release position in response to engagement of the end effector with the buttress applier cartridge, wherein the actuator sled in the restraint position is configured to capture the first buttress assembly relative to the platform, and wherein the actuator sled in the release position is configured to release the first buttress assembly from the platform and allow the end effector to remove the first buttress assembly therefrom.

\* \* \* \* \*